US007624027B1

(12) United States Patent
Stern et al.

(10) Patent No.: US 7,624,027 B1
(45) Date of Patent: Nov. 24, 2009

(54) METHOD AND SYSTEM FOR AUTOMATED MEDICAL RECORDS PROCESSING

(75) Inventors: David E. Stern, Caledonia, IL (US); Wayne R. Pearson, Crystal Lake, IL (US); John J. Koehler, Caledonia, IL (US)

(73) Assignee: Practice Velocity, LLC, Belvidere, IL (US)

( * ) Notice: Subject to any disclaimer, the term of this patent is extended or adjusted under 35 U.S.C. 154(b) by 1455 days.

(21) Appl. No.: 10/692,976

(22) Filed: Oct. 24, 2003

Related U.S. Application Data

(60) Provisional application No. 60/422,083, filed on Oct. 29, 2002.

(51) Int. Cl.
*G06Q 50/00* (2006.01)
*G06F 19/00* (2006.01)

(52) U.S. Cl. .............................................. 705/2; 705/3
(58) Field of Classification Search ....................... 705/2
See application file for complete search history.

(56) References Cited

U.S. PATENT DOCUMENTS

| 3,714,486 A | 1/1973 | McCrary |
| 3,783,251 A | 1/1974 | Pavkovich |
| 3,783,288 A | 1/1974 | Barbour |
| 3,839,708 A | 10/1974 | Bredesen |
| 3,946,236 A | 3/1976 | Roberts |
| 4,290,114 A | 9/1981 | Sinay |
| 4,315,309 A | 2/1982 | Coli |
| 4,408,181 A | 10/1983 | Nakayama |
| 4,489,387 A | 12/1984 | Lamb |
| 4,491,725 A | 1/1985 | Pritchard |
| 4,553,206 A | 11/1985 | Smutek |
| 4,630,274 A | 12/1986 | Schafer |
| 4,658,370 A | 4/1987 | Erman |
| 4,667,292 A | 5/1987 | Mohlenbrock |
| 4,711,996 A | 12/1987 | Drexler |
| 4,745,268 A | 5/1988 | Drexler |
| 4,803,641 A | 2/1989 | Hardy |
| 4,835,372 A | 5/1989 | Gombrich |
| 4,857,713 A | 8/1989 | Brown |

(Continued)

OTHER PUBLICATIONS

Newman, A desk supporting computer-based interaction with paper documents, Conference on Human Factors in Computing Systems, Proceedings of the SIGCHI conference on Human factors in computing systems, Monterey, California, United States, pp. 587-592, Year of Publication: 1992, ISBN:0-89791-513-5.*

(Continued)

*Primary Examiner*—C. Luke Gilligan
*Assistant Examiner*—Tran Nguyen
(74) *Attorney, Agent, or Firm*—Lesavich High-Tech Law Group, P.C.; Stephen Lesavich

(57) ABSTRACT

A method and system for automated medical records processing. The method and system includes plural paper and electronic templates specifically designed such that they reduce the complexity of collecting patient encounter information and help generate the appropriate number and type medical codes for a specific type of medical practice when processed. The method and system also includes processing applications that allow easy and automated collection, processing, displaying and recording of medical codes (e.g., diagnosis codes, billing codes, insurance codes, etc.). The medical codes and other types of processed patient encounter information are displayed in real-time on electronic templates immediately after a patient encounter.

17 Claims, 15 Drawing Sheets

U.S. PATENT DOCUMENTS

| | | |
|---|---|---|
| 4,857,716 A | 8/1989 | Gombrich |
| 4,858,121 A | 8/1989 | Barber |
| 4,878,175 A | 10/1989 | Norden-Paul |
| 4,937,743 A | 6/1990 | Rassman |
| 4,987,538 A | 1/1991 | Johnson |
| 5,001,630 A | 3/1991 | Wiltfong |
| 5,002,630 A | 3/1991 | Kermani |
| 5,018,067 A | 5/1991 | Mohlenbrock |
| 5,065,315 A | 11/1991 | Garcia |
| 5,070,452 A | 12/1991 | Doyle |
| 5,072,383 A | 12/1991 | Brimm |
| 5,077,666 A | 12/1991 | Brimm |
| 5,099,424 A | 3/1992 | Schneiderman |
| 5,148,366 A | 9/1992 | Buchanan |
| 5,225,976 A | 7/1993 | Tawil |
| 5,235,507 A | 8/1993 | Sackler |
| 5,235,702 A | 8/1993 | Miller |
| 5,253,164 A | 10/1993 | Holloway |
| 5,301,105 A | 4/1994 | Cummings |
| 5,307,262 A | 4/1994 | Ertel |
| 5,319,543 A | 6/1994 | Wilhelm |
| 5,324,077 A | 6/1994 | Kessler |
| 5,325,293 A | 6/1994 | Dorne |
| 5,359,509 A | 10/1994 | Little |
| 5,365,425 A | 11/1994 | Torma |
| 5,392,209 A | 2/1995 | Eason |
| 5,404,292 A | 4/1995 | Hendrickson |
| 5,420,409 A | 5/1995 | Longacre |
| 5,465,082 A | 11/1995 | Chaco |
| 5,467,268 A | 11/1995 | Sisley |
| 5,471,382 A | 11/1995 | Tallman |
| 5,482,008 A | 1/1996 | Stafford |
| 5,483,443 A | 1/1996 | Milstein |
| 5,486,999 A | 1/1996 | Mebane |
| 5,490,196 A | 2/1996 | Rudich |
| 5,504,796 A | 4/1996 | Da Silveira |
| 5,510,606 A | 4/1996 | Worthington |
| 5,519,607 A | 5/1996 | Tawil |
| 5,557,514 A | 9/1996 | Seare |
| 5,583,758 A | 12/1996 | McIlroy |
| 5,583,760 A | 12/1996 | Klesse |
| 5,621,779 A | 4/1997 | Hughes |
| 5,644,778 A | 7/1997 | Burks |
| 5,661,291 A | 8/1997 | Ahearn |
| 5,663,999 A | 9/1997 | Siochi |
| 5,664,109 A | 9/1997 | Johnson |
| 5,664,207 A | 9/1997 | Crumpler |
| 5,671,282 A | 9/1997 | Wolff |
| 5,672,154 A | 9/1997 | Sillen |
| 5,700,998 A | 12/1997 | Palti |
| 5,724,379 A | 3/1998 | Perkins |
| 5,754,622 A | 5/1998 | Hughes |
| 5,772,585 A | 6/1998 | Lavin |
| 5,819,228 A | 10/1998 | Spiro |
| 5,832,447 A | 11/1998 | Rieker |
| 5,835,897 A | 11/1998 | Dang |
| 5,842,976 A | 12/1998 | Williamson |
| 5,845,253 A | 12/1998 | Rensimer |
| 5,845,254 A | 12/1998 | Lockwood |
| 5,845,269 A | 12/1998 | Kortge |
| 5,848,426 A | 12/1998 | Wang |
| 5,867,553 A | 2/1999 | Gordon |
| 5,915,241 A | 6/1999 | Giannini |
| 5,923,014 A | 7/1999 | Szymusiak |
| 5,924,074 A * | 7/1999 | Evans .......................... 705/3 |
| 5,930,759 A | 7/1999 | Moore |
| 5,953,704 A | 9/1999 | McIlroy |
| 5,970,463 A | 10/1999 | Cave |
| 5,971,279 A | 10/1999 | Raistrick |
| 5,979,757 A | 11/1999 | Tracy |
| 6,159,013 A | 12/2000 | Parienti |
| 6,192,400 B1 | 2/2001 | Hanson |
| 6,208,973 B1 | 3/2001 | Boyer |
| 6,222,452 B1 | 4/2001 | Ahlstrom |
| 6,342,839 B1 | 1/2002 | Curkendall |
| 6,347,329 B1 | 2/2002 | Evans |
| 6,366,651 B1 | 4/2002 | Griffith |
| 6,370,511 B1 | 4/2002 | Dang |
| 6,393,404 B2 | 5/2002 | Waters |
| 6,464,136 B2 | 10/2002 | Walsh |
| 6,497,358 B1 | 12/2002 | Walsh |
| 6,529,876 B1 * | 3/2003 | Dart et al. ....................... 705/4 |
| 6,592,517 B2 | 7/2003 | Pratt |
| 6,597,948 B1 | 7/2003 | Rockwell |
| 6,603,464 B1 | 8/2003 | Rabin |
| 6,637,649 B2 | 10/2003 | Walsh |
| 6,655,583 B2 | 12/2003 | Walsh |
| 6,824,052 B2 | 11/2004 | Walsh |
| 6,830,180 B2 | 12/2004 | Walsh |

OTHER PUBLICATIONS

Newman, A desk supporting computer-based interaction with paper documents, Conference on Human Factors in Computing Systems, Proceedings of the SIGCHI conference on Human factors in computing systems, Monterey, California, United States, pp. 587-592, Year of Publication: 1992, ISBN:0-89791-513-5.*

* cited by examiner

FIG. 2A (Medical intake form — General PIVoT™ Ver. 0017 08/31/03)

Header fields: First Name, MI, Last Name; Social Security / Patient Account Number; Date of Birth (mm-dd-yyyy); Today's Date (mm-dd-yy); Visit Time (hh-mm); AM/PM; PV TEST PRACTICE 9999, 303A ANDREWS DR., BELVIDERE, IL 61008

Checkboxes (right side): Can, Rescan, No Code, Discard
Checkboxes (left side): Trans, Phys

Main Problem (choose only one)
- ☐ pain  ☐ pressure  ☐ vomiting  ☐ nausea
- ☐ numbness  ☐ itching  ☐ diarrhea  ☐ anxiety/nerves
- ☐ swelling  ☐ congestion  ☐ cough  ☐ depression
- ☐ other (specify) _____

Where is it? _____
For about how long? ___ hr ___ day ___ mo ___ yr
Worse when _____
Better when _____
It is... ☐ constant  ☐ constant, worse at times  ☐ comes & goes
List related symptoms _____
How severe? ☐0 ☐1 ☐2 ☐3 ☐4 ☐5 ☐6 ☐7 ☐8 ☐9 ☐10 (check one) (little pain or symptoms / worst of your life=10)
Additional Description _____
Was this a result of an injury? ☐ no  ☐ yes (describe below)
Motor vehicle accident? ☐ no  ☐ yes    Work-related? ☐ no  ☐ yes

Medical Prob | Medications (dose, freq) | Past Surgeries
- ☐ None | ☐ None | ☐ None (surgery & date)
- ☐ heart disease
- ☐ lung disease
- ☐ diabetes
- ☐ cancer (specify)
- ☐ seizures
- ☐ hay fever
- ☐ high blood press

Family History: illnesses occurring before age 65
- Father  ☐ none _____
- Mother  ☐ none _____
- Siblings ☐ none _____
- Children ☐ none _____

Tobacco ☐ never | quit in (yr) ___ | ☐ cigars
packs per day ☐ <1/2  ☐ <1  ☐ 1  ☐ 1 1/2  ☐ >2  ☐ chew or snuff
Alcohol ☐ never  drinks per day ☐ <1  ☐ 1-2  ☐ 1 1/2  ☐ >2
Illicit Drugs? ☐ no  ☐ yes    patent pending © 2003 Practice Velocity

Recent Abnormal (for you) Symptoms | None
- Const ☐
- Neuro ☐
- Head ☐ (pain in →)
- Eyes ☐
- Skin ☐
- Musc-Skel ☐ (muscle pain → / joint pain →)
- Cardio ☐
- Resp ☐
- G.I. ☐
- Genito-Urinary ☐
- Endo ☐
- Psych ☐
- Heme ☐
- Allergy ☐

Allergies (Document in boxes below) _____
Pregnant? ☐ Yes  ☐ No  ☐ Unsure
Last Menses ___ - ___ - ___ (mm-dd-yy)
Last Tetanus Booster ___ - ___ - ___ (mm-dd-yy)

Quality Verification
Sign in Complete → Sign out Complete → PIVoT™ Scanned 0001051
36849

FIG. 3
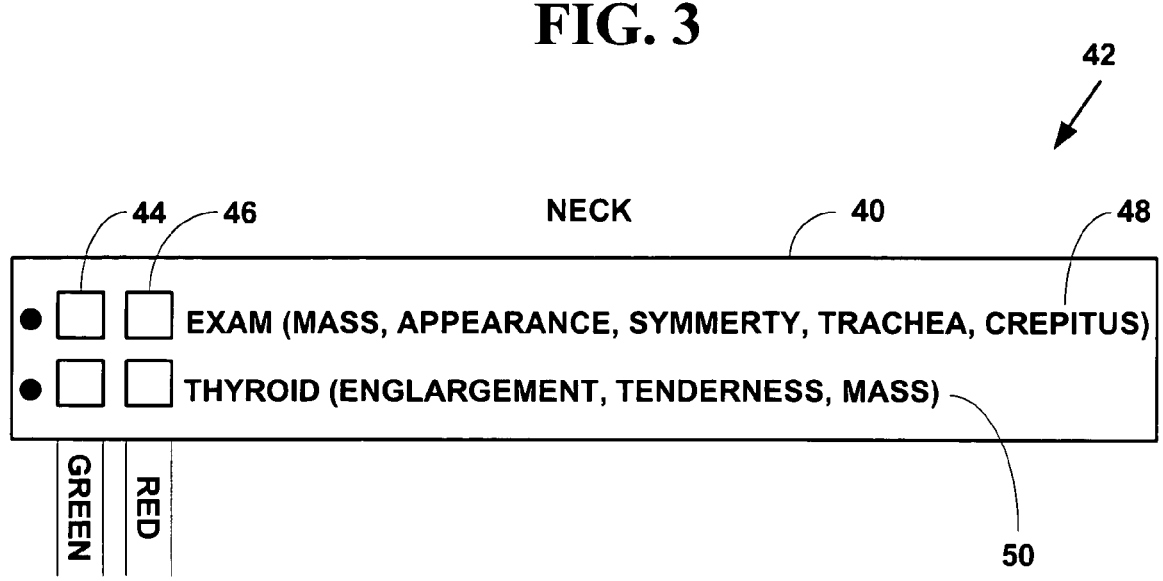
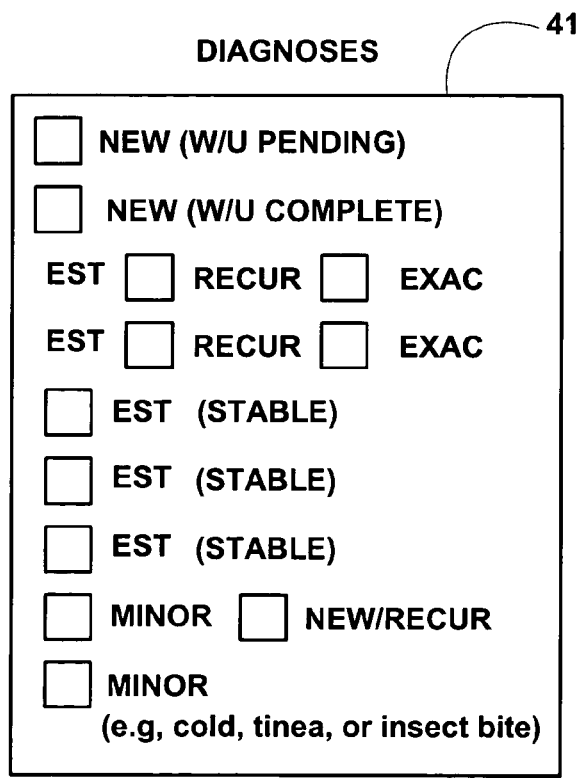

HX _____ (pick lowest)

|      | CC | HPI | PFMSH | ROS |
|------|----|-----|-------|-----|
| PF   |    | 0   | 0     | 0   |
| EXPF |    | 1   | 1     | 1   |
| DET  |    |     |       | 2   |
| COMP | 1  | 4   | 2,3   | 10  |

PX _____

| PF   | 1 bullet                        |
| EXPF | 6 bullets                       |
| DET  | 12 bullets (2 systems)          |
| COMP | ≥2 bullets each in ≥9 systems   |

CX _____ (pick lowest)

|      | DX | RISK |
|------|----|------|
| HIGH | 4  | 4    |
| MOD  | 3  | 3    |
| LOW  | 2  | 2    |
| SF   | 1  | 1    |

FIG. 11

Final E/M  NEW OUTPATIENT                                  130

|    | 99201 | 99202 | 99203 | 99204 | 99205 |
|----|-------|-------|-------|-------|-------|
| HX | PF    | EXPF  | DET   | COMP  | COMP  |
| PX | PF    | EXPF  | DET   | COMP  | COMP  |
| CX | SF    | SF    | LOW   | MOD   | HIGH  |

FIG. 12

Final E/M  ESTABLISHED OUTPATIENT                          132

|    | 99212 | 99213 | 99214 | 99215 |
|----|-------|-------|-------|-------|
| HX | PF    | EXPF  | DET   | COMP  |
| PX | PF    | EXPF  | DET   | COMP  |
| CX | SF    | LOW   | MOD   | HIGH  |

METHOD AND SYSTEM FOR AUTOMATED MEDICAL RECORDS PROCESSING

CROSS REFERENCES TO RELATED APPLICATIONS

This U.S. Non-Provisional Patent Application claims priority from U.S. Provisional Patent Application No. 60/422,083, filed on Oct. 29, 2002, the contents of which are incorporated herein by reference.

FIELD OF THE INVENTION

This invention relates to medical records and information. More specifically, it relates to a method and system for automated medical records processing.

BACKGROUND OF THE INVENTION

There are many different types of medical information that are routinely collected when a patient has an emergency or non-emergency medical problem, or visits a provider for a routine visit or annual physical. The medical information includes such information as current symptoms the patient is feeling, any medication the patient is currently taking, any past medical problems or surgeries the patient has, known allergies, family history, prescribed medications, etc.

Such medical information is typically recorded manually on paper forms by medical staff, nurses and/or providers. The medical information may also be dictated by a provider and later transcribed to another form by a medical transcriptionist.

The American Medical Association ("AMA") has developed a system of codes for medical and surgical procedures, diagnostic tests, laboratory studies, and other provider medical services rendered to patients. This system of codes is referred to as Current Procedural Terminology, ("CPT") codes. CPT codes provide a uniform language that details medical, surgical, and diagnostic services utilized by providers to communicate to third-party payors for the services that are rendered.

The CPT codes were first developed by the AMA in 1966. Each year, an annual publication is prepared by the AMA that includes CPT code changes corresponding with updates in medical technology and practice. The 2003 version of CPT codes, for example, CPT 2003, includes over 8,000 codes and descriptors. The CPT code set also includes a set of modifiers that may be used to further define CPT codes.

Evaluation and Management (E/M) codes are a sub-set of the CPT codes that are used to describe a patient's encounter in a provider's office, hospital or other medical setting. E/M codes are used to describe the level of care a provider renders to a patient.

The CPT and E/M codes are assigned numeric codes that used to classify the information, categorize and organize the information and used to generate revenue for the organization that employs the medical personnel. The numeric codes may also include codes used by insurance companies or other types of organizations such as health organizations such as those responsible for communicable diseases. Additional information on the AMA CPT and E/M codes can be obtained on the Internet at the Universal Resource Locator ("URL") "www.ama-assn.org."

The Health Care Finance Administration ("HCFA"), a U.S. government agency responsible for the operation of oversight of medical insurance programs such as Medicare and Medicaid, has also developed a set of medical codes and modifiers. The HCFA developed a set of medical codes called Health Care Procedural Coding System ("HCPCS") codes to help relate CPT codes to medical billing. The HCFA was renamed the Centers for Medicare & Medicaid Services (CMS) on Jun. 14, 2001. Additional information on the HCFA HCPCS codes can be found on the Internet at the URL "cms.hhs.gov."

In addition, the World Health Organization ("WHO") also developed a similar set of codes to identify medical diagnoses, conditions and injuries. These codes are called International Classification of Diseases 9th edition Clinical Modification ("ICD-9") codes and International Classifications $10^{th}$ edition Clinical Modification ("ICD-10") can be found on the internet at the URL "www.who.org". ICD-10 codes for both diagnoses and procedures have been developed, but are not yet used in the USA.

Accurate and proper coding of medical information is important because it helps determine financial reimbursement for physician services. It is also important to ensure compliance with state and federal regulations as well as help protect physicians from the financial and legal ramifications of government, insurance company and other types of audits.

There are many problems associated with the collection and recording medical information. One problem is that incorrect medical coding creates both a revenue generation problem and a compliance problem for many physician practices.

For example, one study by Mitchell S. King, Lisa Sharp, and Martin S. Lipsky, entitled "Accuracy of CPT evaluation and management coding by family physicians," and published in the Journal of American Board of Family Practice 14(3):184-192, 2001, has shown that family physicians tend to generate lower-level E/M codes for established patients, thereby "undercoding" the established patient visit. The undercoding results in a loss of potential revenues. Investigative agencies may also classify this practice as fraudulent, in that it may be construed to indicate that the provider is reducing fees by undercoding, and thereby attempting to entice patients to visit more frequently.

These same family physicians also tend to generate higher-level E/M codes than necessary for new patients, thereby "overcoding" the new patient visit. This results in rejection of insurance payments and could result in loss of revenue, insurance audits and potential prosecution under the Federal False Claims Act ("FFCA"), 31 U.S.C. 3729 or other Federal and state laws used prevent fraudulent insurance claims.

Another problem is that incorrect or improper coding of medical information could result in non-compliance with the Health Insurance Portability and Accountability Act ("HIPAA") 42 U.S.C. 1320d, et. seq. and other Federal and state laws enacted to protect privacy.

Another problem is that medical organizations use many different types of medical codes from many different types of medical organizations on many different types of proprietary and public medical forms. The medical information is typically manually re-handled several times by several different types of people (e.g., providers, nurses, medical billing specialist, etc.) with different expertise levels with respect to coding of medical information. This handling may introduce errors for the coding of medical information at many different levels.

Another problem is that the medical information is often manually entered into a data processing system. A medical technician with knowledge of medical information and medical codes must process the information to assign the proper codes. As was described above, there are typically multiple sets of medical codes such as those used for diagnosis, billing, insurance, etc. that are routinely used and changed on a periodic basis. This may also introduce errors for the coding of medical information at many different levels.

Another problem is that it typically takes a significant amount of time to process medical information and create the proper medical codes from a patient encounter. This often leads to a very slow revenue stream for physicians and a large amount of frustration for patients.

There have been attempts to solve one or more of the problems associated with coding medical information. For example, U.S. Pat. No. 6,529,876 to Dart et al. entitled "Electronic template medical records coding system" describes a method and a computer program for use by health care providers for the production of accurate billing coding for care entered using established E/M codes.

U.S. Pat. No. 6,393,404 to Waters, et al. entitled "System and method for optimizing medical diagnosis, procedures and claims using a structured search space" describes a system and method for optimizing medical diagnosis, procedures and reimbursement claims using a structured search space.

U.S. Pat. No. 6,208,973 to Boyer, et al. entitled "Point of service third party financial management vehicle for the healthcare industry" describes a point of service third party adjudicated payment system and method which provides for the creation of an adjudicated settlement transaction at a point of service which designates the portion of the service to be paid by the third party payor and the portion to be paid by the customer.

U.S. Pat. No. 5,483,443 to Milstein, et al. entitled "Method for computing current procedural terminology codes from physician generated documentation" describes a process for calculating a Current Procedural Terminology ("CPT") code from input received from a physician or other medical professional.

However, these inventions do not solve all of the problems associated with coding medical information. Thus, it would be desirable to help reduce the complexity of collecting patient encounter information and allow easy automated collection, processing and recording of medical information codes such as diagnosis codes, billing codes, insurance codes, etc. It is also desirable to provide such medical codes in real-time during or shortly after an encounter with a patient.

SUMMARY OF THE INVENTION

In accordance with preferred embodiments of the present invention, some of the problems associated with processing medical records are overcome. A method and system for automated medical records processing is presented.

The method and system includes plural paper information templates specifically designed such that they may help reduce the complexity of collecting patient encounter information and help generate the appropriate type and number medical codes for a specific type of medical practice when processed.

The method and system also includes real-time processing applications that may allow easy and automated collection, processing, displaying and recording of medical codes (e.g., diagnosis codes, billing codes, insurance codes, etc.).

The foregoing and other features and advantages of preferred embodiments of the invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIGS. 2A and 2B are block diagrams illustrating a front side and a back side of an exemplary paper medical information template;

FIGS. 2C and 2D are a block diagram illustrating a front side and a back side of another exemplary paper medical information form that further illustrates an exemplary coding summary produced from exemplary patient encounter information;

FIG. 3 is a block diagram illustrating portions of the exemplary paper medical information template of FIG. 2;

FIG. 11 is a block diagram illustrating an exemplary final E/M matrix for a new outpatient;

FIG. 12 is a block diagram illustrating an exemplary final E/M matrix for an established outpatient;

DETAILED DESCRIPTION OF PREFERRED EMBODIMENTS

Medical Records System

Figure 1:
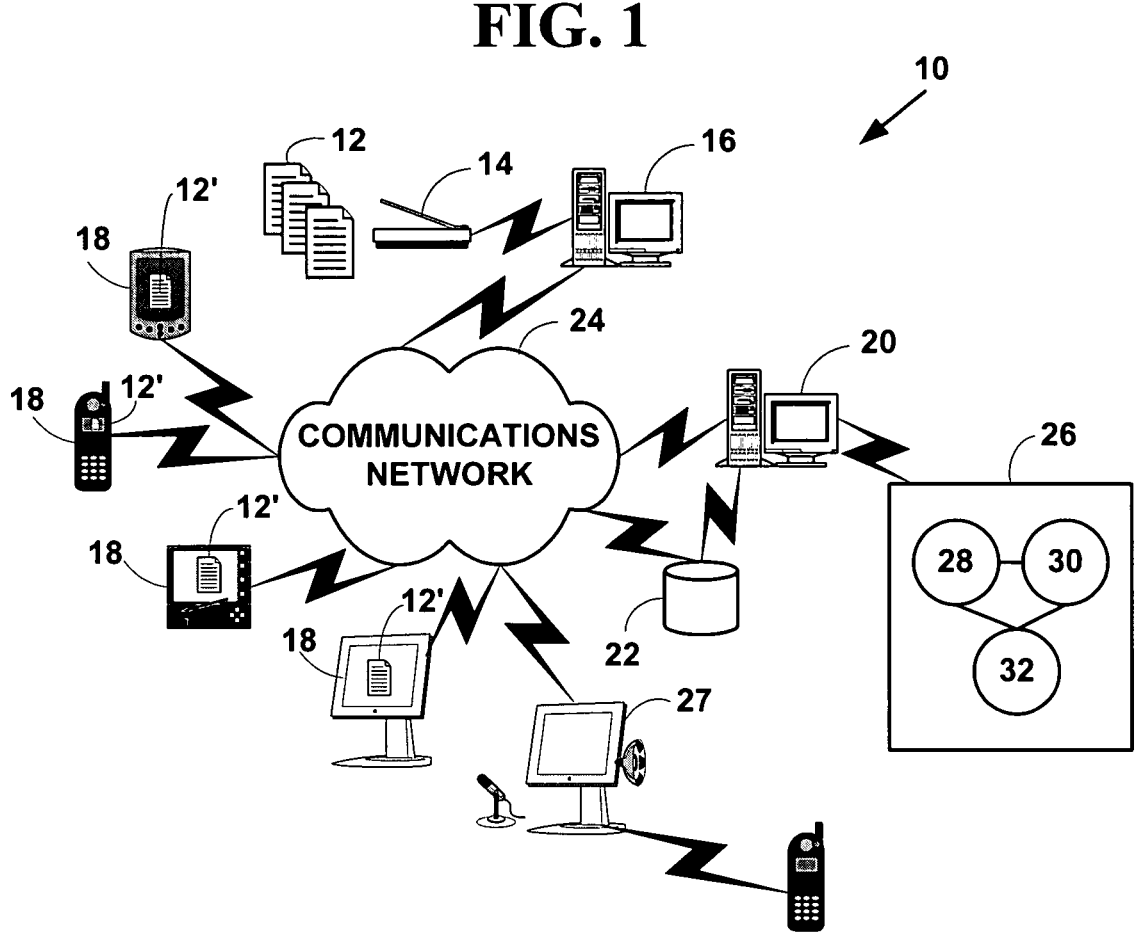
FIG. 1 is a block diagram illustrating an exemplary medical records system.

FIG. 1 is a block diagram illustrating an exemplary medical records system 10. The medical records system 10 includes plural medical information templates, including plural paper 12 and plural electronic medical information templates 12', one or more electronic scanners 14 (one illustrated), one or more client computers 16 (one illustrated), one or more client electronic devices 18, one or more server computers 20 (one illustrated), and one or more databases 22 (one illustrated). The components of the medical records system 10 communicate via a communications network 24. However, the present invention is not limited to these components, and more, fewer or other components can also be used to practice the invention.

The one or more client electronic devices 18 include plural software applications for displaying an electronic medical information template 12', collecting digital information from the electronic medical information templates 12', encrypting the collected digital information, for compressing and packaging the encrypted digital information and for securely transmitting the encrypted, compressed and packaged digital information. The one or more client electronic devices 18 may also include the medical data presentation application 32 described below. However, the one or more electronic client devices 18 are not limited to these, and more, fewer or other components can also be used on the one or more client electronic devices 18.

The client computers 16 include plural software applications for scanning in paper medical information templates 12 from scanner 14 and creating one or more digital images, for encrypting the digital images created, for compressing and packaging the encrypted digital images and for securely transmitting the encrypted, compressed and packaged digital images. The client computers 16 may also include the medical data presentation application 32 described below. However, the client computers 16 are not limited to these, and more, fewer or other components can also be used on the client computers 16. The client computers 16 may be local or remotely located with respect to the scanner 14.

The server computers 20 include comprising plural processing applications 26. The plural processing applications 26 include, but are not limited to, a medical information template reader application 28, a medical code processing engine 30, a medical data presentation application 32 and a digital image verification application 33. However, the present invention is not limited to such applications, and more, fewer or other software applications can also be used on the server computer 20. In one embodiment of the invention, the plural processing applications are software applications. However, the plural processing applications 26 can also include plural software, firmware, hardware applications an/or combinations thereof and the present invention is not limited to software processing applications. The server computers 20 may be local or remote to the client computers 16 and electronic client devices 18.

The database 22 comprises a relational database. However, the present invention is not limited to a relational database and other types of databases can also be used. The communications network 24 includes a wired or wireless communications network including components of the Public Switched Telephone Network ("PSTN"), the Internet, intranets, or types of wired or wireless, including voice and data communications networks, and including local area networks ("LAN") and wide area networks ("WAN").

The medical records system further includes a secure audio dictation interface 27. The audio dictation interface 27 allows a provider to securely access the medical records system 10 (e.g., via a secure web-page, secure dial-in, secure voice-mail, etc.) and dictate audio information via a microphone such as those attached to a computer, mobile phone, personal digital assistant ("PDA"), etc. The dictated audio information is then stored in database 22 as an audio file in an appropriate audio format (e.g., a MIDI, WAVE, MP3, or other audio format). The audio dictation interface 27 also allows a medical transcriptionist to securely access a saved audio file and transcribe the audio information into electronic text. The electronic text is saved in database 22 and is associated with an electronic medical record created for a patient encounter as is explained below.

An operating environment for components of the medical records system 10 include a processing system with one or more high speed Central Processing Unit(s) ("CPU") and a memory. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU executed" or "processor executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected or distributed computer readable medium, which exist exclusively on the processing system or be distributed among multiple interconnected processing systems that may be local or remote to the processing system and may be accessed by one or more CPUs or processors.

Medical Information Templates

Figure 2B:
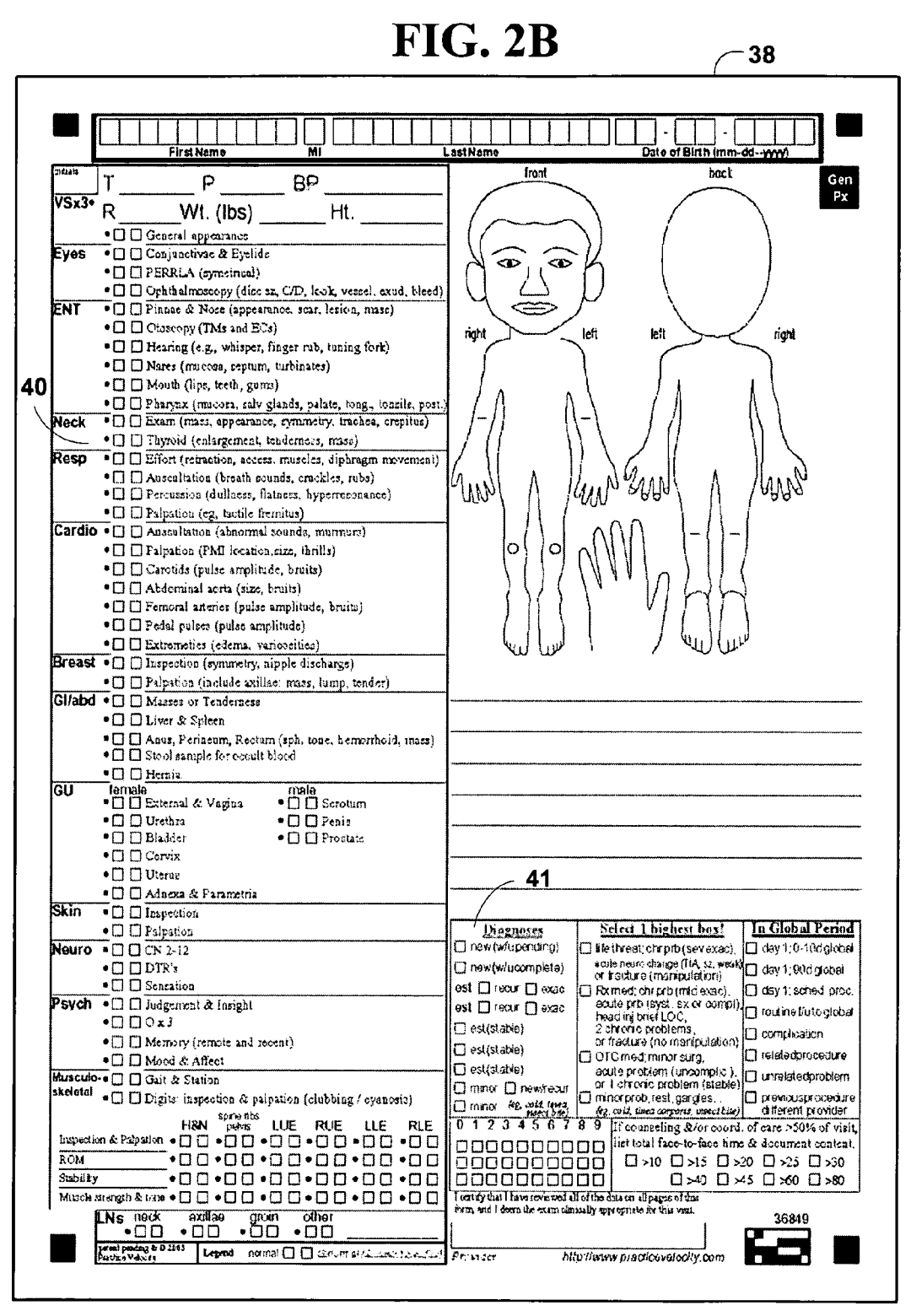

FIGS. 2A and 2B are a block diagram illustrating an exemplary paper medical information template 34 including a front side 36 (FIG. 2A) and a back side 38 (FIG. 2B). Exemplary paper medical information template 34 is an exemplary medical information template 34 from the set of plural paper 12 and electronic 12' medical information templates used, for example, in an emergency room or walk-in clinic or for any appropriate medical practice. Such a paper information template 34 is used by providers and other clinical personnel to complete documentation of history, physical exam, complexity of medical decision making, and other relevant information for an encounter with a patient.

The plural medical information templates 12 also include specialized paper medical information templates (not illustrated) such as those used for pediatrics, obstetrics and gynecology, cardiology, neurology, etc. Such specialized paper medical information templates are configured and laid out similar to the exemplary paper medical information template 34 of FIG. 2 and are used to complete documentation for history, physical exam, complexity of medical decision making and other relevant information in a specialized area of medicine (e.g., for a physician with a specialized medical practice).

The plural medical information templates also include general and specialized electronic medical information templates 12' that can be displayed and used on desktop and handheld electronic devices 18. The electronic medical information templates 12' can be displayed on desktop electronic devices such as computers, etc. or other types of desktop electronic devices 18. The electronic medical information templates can also be displayed and used on hand-held electronic devices, such as, personal digital/data assistants ("PDA"), electronic tablets, Internet appliances, mobile phones or other types of handheld electronic devices 18.

The paper medical information template 34 is designed such that the plural processing applications 26 may read and/or interpret data from a digital image made of a paper copy of a medical information template 34, or directly from electronic medical information templates 12' created for an electronic device.

The paper medical information template 34 includes a limited number of check boxes, blanks and diagrams or other pre-denoted fields to fill in. The limited number of choices helps reduce the amount and/or complexity of data to be reviewed and the number of diagnostic options to be considered while at the same time helping ensure the appropriate number and type medical codes will be generated for the patient encounter.

The medical information templates 12, 12' including exemplary paper medical information template 34, are not used as documents where diagnostic information is entered by a provider or other clinical personnel, where the responsibility for deciphering and selecting the appropriate codes is then performed directly by a physician or transferred to a person with knowledge of medical coding and medical codes (corresponding to various diagnoses, procedures or services), who manually enters the appropriate medical codes into a document or a medical records systems.

Instead, the plural medical information templates 12, 12' are designed and laid out in a format that systematically documents the specific information, corresponding to medical codes that are a collection of the most common and most likely to encountered for a specific type of general or specialized medical practice. By simply completing the medical information templates 12, 12' during a patient encounter, the physician (or other skilled medical personnel such as nurses, physician assistants, etc.) will cause many, if not all, of the proper medical coding to be automatically generated when the electronic images of the templates are processed by the medical records system 10.

When they are processed by the medical records system 10, the plural medical information templates 12, 12' allow automatic generation and display in real-time, of the proper medical and insurance codes typically used by medical and health care providers for general and specific types of medical diagnosis's (e.g., emergency room or walk-in clinic diagnosis, specialized medical practices, etc.). The design and layout of the plural medical information templates 12, 12' also allows automatic easy and efficient processing by the medical records system 10 and other types of data processing systems such as billing and invoicing systems The plural medical information templates 12, 12' may simplify documentation using any of the following methods: (1) reducing the complexity associated with choosing the correct level of medical decision making by allowing only a small number of check boxes (or other easily-denoted fields) for each level of risk; (2) eliminate the use of amount and/or complexity of medical data to be reviewed. Selected data may be eliminated on templates designed for practices where extensive review of such data is very rare. However, check boxes (or other easily-denoted fields) for other data may be placed on templates for medical practices where use of this category is helpful for determining a proper level of CPT E/M coding; (3) limiting and categorizing a number of diagnoses or management options. Check boxes (or other easily-denoted fields) are used directly for categorizing the number of diagnoses or management options. The check boxes (or other easily-denoted fields) are limited in number to those in each category allowed by current coding guidelines. The provider may check as many as possible, but can not check too many, as the check boxes on the template are limited as noted above; (4) electronically process, display and utilize in real-time patient encounter information recorded on a paper medical template 12 after the paper medical template has been converted into a digital image; (5) help electronically process, display, and utilize in real-time data recorded on electronic medical templates 12' after the electronic medical information template has been processed; and (6) allow easy changes of coding definitions. If coding definitions are changed by any entity, changes are easily made within the method and system.

FIG. 2B also includes an exemplary information area 40 with four check-boxes for the Neck as is explained in connection with FIG. 3. In addition, FIG. 2B illustrates an exemplary information area 41 with plural check boxes for completing a medical diagnosis as is explained below in connection with Table 3.

FIG. 3 is a block diagram 42 illustrating portions of the exemplary paper medical information template 34 from FIG. 2B. For example, the exemplary paper medical information template 34 on its back side 38 (FIG. 2B) includes a box labeled "Neck" 40 and a box labeled "Diagnoses" 41.

A Neck box 40 (FIG. 3) includes two columns of check boxes 44, 46 typically identified by colors including for example, green and red. The green check box is the first or leftmost check box and the red check box is the second or rightmost check box. The green check box indicates the provider examined the patient, but the patient does not have any abnormality in the indicated body area or system. The red check box indicates the provider examined the patient, but the patient does have one or more abnormalities in the indicated body area or system. However, the exemplary paper medical information template 34 is not limited to such check boxes and other colors, other designations and other layouts for the check boxes can also be used.

For example, the Neck box 40 includes a first row 48 labeled "Exam (mass, appearance, symmetry, trachea, crepitus)" and a second row 40 labeled "Thyroid (enlargement, tenderness, mass)."

The information in these rows may include some or all of the specified physical exam items from the published guidelines for CPT E/M codes related to the neck. Thus, a physicians (or other skilled medial personnel) with no knowledge or a large amount of knowledge of medical coding practices can use the medical information template efficiently. In both situations, the proper medical codes are generated automatically for the patient encounter. Coding is not based on the coding knowledge of the provider (or other skilled medical personnel), but rather on the actual documentation of the encounter on the patient's medical record.

During an examination of the patient, the provider might check the patient's neck if the patient was in an automobile accident or otherwise complained of neck pain. If the patient's neck exam was normal, the physical would check the green check box column 44 of the first row 48 in the Neck box 38. (See FIG. 2D).

If the patient's neck exam was abnormal, the provider would check the red check box column 46 of the first row 48 in the Neck box 40.

The provider need not specify and document the actual abnormality using handwritten, typed text, voice dictation, or choose from a list of specific abnormal conditions. A similar procedure would be followed during the examination of the patient's Thyroid in the second row 50 of the Neck box 40.

Diagnoses box 41 includes check boxes for new and established diagnoses. It also includes a range of possible levels of medical diagnoses from minor to complex as is explained below.

The plural medical information templates 12, including exemplary paper medical information template 34, are scanned into the medical records system 10 via scanner 14. Patient encounter information is collected from the plural electronic medical information templates 12' via a number of other methods via a communications connection established with the server computers 20 via the communications network 24 (e.g., infrared connection, or other wired or wireless connection via a Personal Digital Assistant ("PDA"), mobile phone, etc.).

The data on the plural medical information templates 12, 12' is used for multiple purposes including (but not limited to):

1. Coding of and/or billing for Evaluation and Management codes ("E/Ms") codes in real-time.
2. Coding of and/or billing for Current Procedural Terminology ("CPTs") codes in real-time.
3. Coding of and/or billing for Health Care Financing Administration Common Procedural Coding System ("HCPCS") codes in real-time.
4. Coding of and/or billing for International Classification of Diseases $9^{th}$ or $10^{th}$ Edition Clinical Modification codes in real-time.
5. Coding of modifiers to be attached to the above-generated codes.
6. Coding of and/or billing for other codes for medical services as defined by governmental agencies, medical associations, insurance companies, other payers, or any other entity that creates or defines codes or a system of codes for the purposes of documenting and/or billing medical services or supplies in real-time.
7. Production of a paper or electronic invoice in real-time immediately after a patient encounter using one or more of the medical codes described in 1-5.
8. Production an electronic medical record in real-time immediately after a patient encounter using or more of the medical codes described in 1-5.
9. Production of other plural electronic templates used to display patient encounter information in real-time.
10. Evaluating the medical data for regulatory compliance (e.g., HIPPA, etc.)
11. Evaluating appropriateness of medical care.
12. Production of text documents through electronic conversion of data on the paper medical record into an electronic medical record.
13. Evaluating patterns of physician practices.
14. Gathering data for medical research.
15. Utilizing generated medical codes in other data processing systems such as other billing and invoicing systems.
16. Other applications deemed appropriate for use of this data while protecting its privacy.

Data Flow in the Medical Records System

Figure 4:
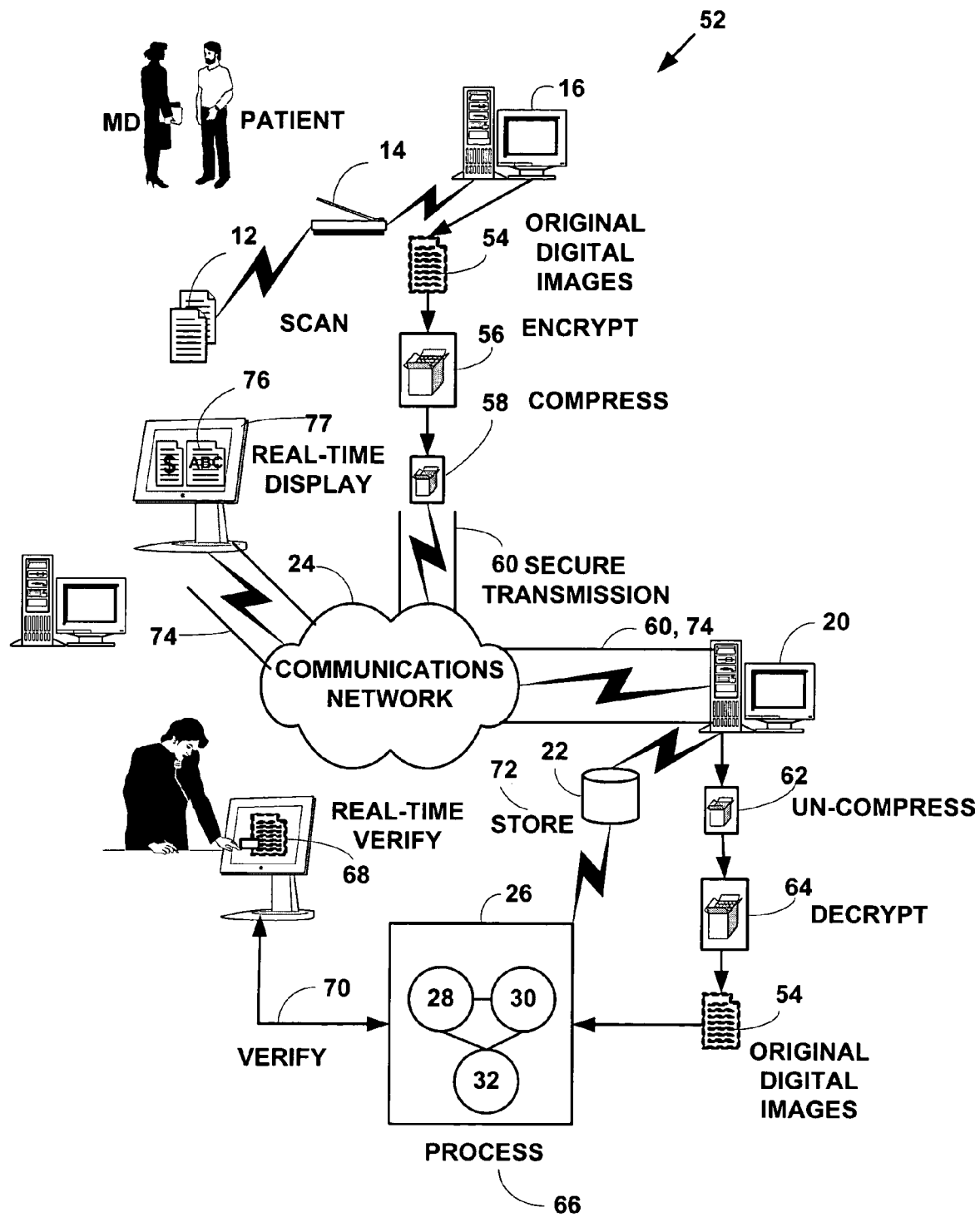
FIG. 4 is a block diagram illustrating an exemplary data flow for the medical records system of FIG. 1 for a paper medical information template.

FIG. 4 is a block diagram illustrating an exemplary data flow 52 for the medical records system 10 for a paper medical information template 12. The data flow 52 includes scanning a paper medical information template 12 (e.g., paper medical information template 34 of FIGS. 2 and 2B) into one or more digital images 54 with a pre-determined image format such as a Tagged Image Format ("TIF") or other types of digital image formats (e.g., Bit Map ("BMP"), Graphics Interchange Format ("GIF"), Joint Pictures Expert Group ("JPEG"), etc.) known in the art, with scanner 14. The paper medical record may also be scanned into other digital formats (e.g., other types of digital data) and the invention is not limited to scan the paper medical information template into a digital image.

The digital images are encrypted 56 to ensure the data it includes is protected and kept private. For example, the digital images may be encrypted using RSA encryption, Data Encryption Standard ("DES") encryption, Advanced Encryption Standard ("AES") encryption, or other encryption methods known in the art.

The encrypted digital images are compressed and packaged 58 to reduce their size and speed up transmission over the communications network 24. For example, the encrypted digital images may be compressed and packaged using PKZIP, by Pkware, Inc. of Brown Deere, Wis., or other types of data compression and data packaging methods known in the art.

The compressed encrypted digital images are securely transmitted 60 over the communications network 24 to the server computer 20. For example, compressed encrypted digital images are securely transmitted via a Secure Sockets Layer ("SSL") (e.g., using an encryption key of 1000-bits or more to protect privacy of the digital images), using the File Transfer Protocol ("FTP").

As is known in the art, a "secure transmission" over a communications network includes a transmission over a communications connection that is protected against unauthorized access, operation, or use, by means of encryption, or other forms of control or security.

However, other secure transmission techniques (e.g., RSA, DES, AES, data encryption, Internet Protocol Security ("IPsec"), etc.) and other data protocols (e.g., Transmission Control Protocol ("TCP")/Internet Protocol ("IP"), User Datagram Protocol ("UDP"), etc.) known in the art can also be used.

The server computer 20 securely receives the compressed encrypted digital images and un-compresses 62 encrypted digital images back to their original size. The server computer 20 decrypts 64 the un-compressed digital images to obtain the original digital images 54 scanned into the medical records processing system 10.

The original digital images 54 are processed 66 by the plural processing applications 26. For example, the medical template reader application 28 extracts patient encounter information from the original digital images 54 and creates a number of internal data structures used to verify and store the patent encounter information as is described below.

In one embodiment of the invention, if the medical template reader application 28 determines that it can not accurately determine specific patient encounter information from the original digital images 54 (e.g., can not electronically scan and process the s or other medical personnel's handwriting, marks on check boxes overlap, etc.), the patient encounter information in question is electronically highlighted on the original digital images 54 and displayed 68 in real-time by the medical data presentation application 32 for a human user to interpret and/or verify 70.

This real-time verification allows errors and/or inconsistencies in electronic interpretation of the data on the digital images to be immediately corrected by a human user. If the digital image is missing necessary, important, required or relevant data (e.g., provider signature, vital signs, patient demographics, etc) this information may be returned to the provider so that the provider appropriately completes this data and the paper template is rescanned.

As is known in the art, "real-time" operations are those in which a computer's systems activities match a human perception of a time period or are computer system operations that proceed at rate similar to an external physical process. In another embodiment of the invention, near real-time or non-real-time processing can also be used.

In another embodiment of invention, if the medical template reader application 28 can not properly determine patient encounter information from the original digital images 54, a determination as a "best guess" is made for the patient encounter information in question using one or more internal (e.g., software 33, hardware, firmware, etc.) digital image analysis techniques available to the medical template reader application 28. This embodiment does not necessarily rely on verification by a human user.

If the medical template reader application 28 has determined patient encounter information from the original digital images 54, and this has been verified and/or corrected by a human user the medical code processing engine 30 automatically generates the appropriate medical codes (e.g., E/M, CPT, HCPCS, etc.) in real-time for the patient encounter information using the internal data structures of stored patient encounter information. The generated medical codes along with the original digital images 54 including the patient encounter information, other patient encounter information extracted and other patient encounter information newly generated (e.g., a new electronic medical information record, an electronic invoice, etc.) are stored 72 in the database 22.

In one embodiment of the invention, the generated medical codes, generated tables of patient encounter information and the original digital images 54 are stored 72 in databases 22, wherein databases 22 are relational databases. The generated medical codes and the original digital images 50 are stored in an open database connectivity ("ODBC") format using structure query language ("SQL") commands to access the databases 22.

However, the invention is not limited to such an embodiment and other types of databases (e.g., non-relational), database formats and database commands can also be used with the databases 22.

As is known in the art, ODBC is standard database access method developed by Microsoft Corporation. ODBC makes it possible to access any data from any application, regardless of which database management system ("DBMS") is handling the data. As is known in the art, SQL is database sublanguage used in querying, updating, and managing relational databases.

The generated medical codes are also used by the medical code processing engine 30 to create an electronic or paper invoice and a summary of the collected medical information for the patient in the form of an electronic medical record in real-time or sent to another data processing system for additional processing The electronic codes and electronic medical record is securely transmitted 74 (e.g., using SSL as described above) and is displayed 76 by the medical data presentation application 32 in real-time for medical office personal. Delayed processing may also be performed as appropriate to the specific situation (e.g., by another data processing system such as an external billing or invoicing system)

The electronic invoice and electronic medical record can be displayed 76 in real-time via the medical data presentation application 32 on the client computers 16 (not illustrated), the server computer 20 (not illustrated), on another secure display 77 in the medical facility that collected medical information form the patient, or by any other authorized user on a computer (not illustrated) equipped for this display.

For example, if a patient entered a clinic and desired to pay by credit card or cash, immediately after being examined by a provider, the patient encounter information recorded on a paper medical information template 12 (e.g., FIG. 2) would be scanned in and processed as just described for FIG. 4. As the patient received his/her exit instructions (e.g., receiving instructions for prescribed medications, instructions to further threat an injury or illness at home, etc.) the medical codes generated in real-time are used to create an electronic invoice in real-time for the patient with an appropriate fee for the patient visit. Thus, the patient can be charged the appropriate fee immediately as he/she is ready to leave the clinic without delaying the patient any significant amount of time. This leads to greater overall patient satisfaction at a time when the patient is in pain or is not otherwise feeling well. This also leads to correct and immediate revenue for the medical facility and/or physician.

The electronic invoice and electronic medical record can also be securely transmitted 74 and displayed 76 at a later time (i.e., non real-time) for medical office personal for patients who are covered by insurance and for physicians who review the patient's chart at a later time.

Figure 5:
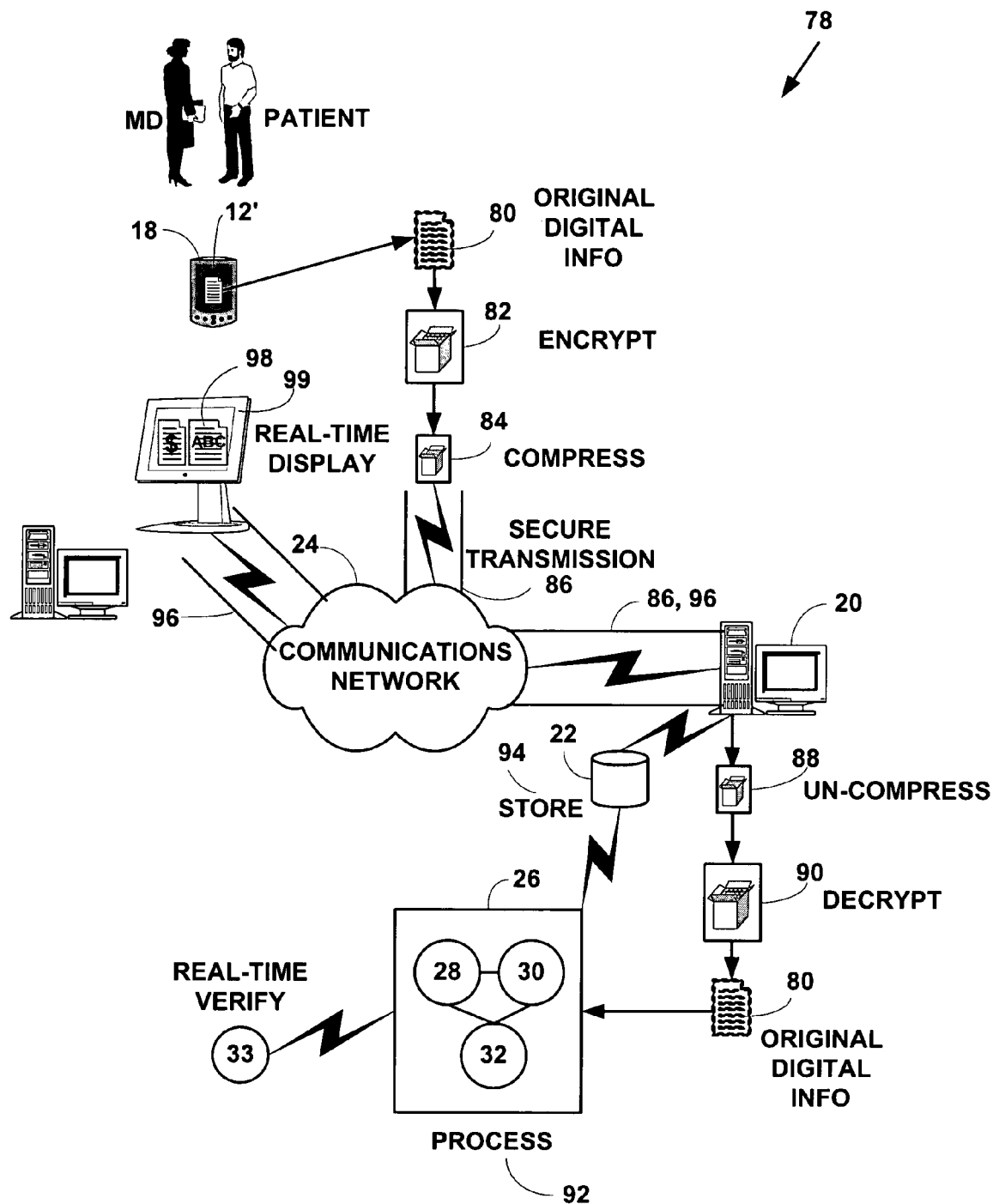
FIG. 5 is a block diagram illustrating an exemplary data flow for the medical records system of FIG. 1 for an electronic medical information template.

FIG. 5 is a block diagram illustrating an exemplary data flow 78 for the medical records system of FIG. 1 for an electronic medical information template 12'. Electronic medical information templates 12' are processed in a manner similar to the paper medical information templates 12 described above. In this embodiment, patient encounter information is not recorded on paper medical information templates. Instead, it is recorded electronically directly on the electronic medical information templates 12'.

The electronic medical information template 12' is displayed on a computer screen or handheld electronic device 18. Digital information 80 from the electronic medical information template 12' is collected and encrypted 82 on the electronic device to ensure the data is protected and kept private.

The encrypted digital information is compressed 84 on the electronic device 18 to reduce its size and speed up transmission over the communications network 24. The compressed encrypted digital information is securely transmitted 86 from the electronic device 18 over the communications network 24 to the server computer 20.

The server computer 20 securely receives the compressed encrypted digital information and un-compresses 88 encrypted digital information back to its original size. The server computer 20 decrypts 90 the un-compressed digital information to obtain the original digital information 80 collected electronically from the electronic device 18, The original digital information 80 is processed 92 by the processing applications 26. The medical template reader application 28 extracts patient encounter information from the original digital information 80 and creates a number of internal data structures used to store the patent information.

In this data flow, the verification steps described above for the paper electronic information templates 12 are typically not necessary because there are no digital images to process, only original digital information 80 generated directly from the electronic medical information template. However, automated internal or human verification may also be performed.

The medical code processing engine 30 automatically generates the appropriate medical codes (e.g., E/M, CPT, HCPCS, etc.) for the patient encounter information using the tables of patient encounter information. The generated medical codes are stored 94 along with the original digital information 80 including the patient encounter information in the database 22.

The generated medical codes are used by the medical code processing engine 30 to create an electronic invoice and an electronic medical record for the patient. The electronic invoice and electronic medical record is securely transmitted 96 (e.g., using SSL as described above) and is displayed 98 by the medical data presentation application 32 in real-time for medical office personal.

The electronic invoice and electronic medical record can be displayed 98 in real-time via the medical data presentation application 32 on the server computer 20 (not illustrated), on another secure display 99 in the medical facility that collected medical information form the patient via the medical data presentation application 32 or on the electronic device 18 from which the patient encounter information was collected (not illustrated).

The electronic invoice and electronic medical record can also be securely transmitted 96 and displayed 98 at a later time (i.e., in non real-time) for medical office personal for patients who are covered by insurance and for physicians who review the patient's chart at a later time. Billing codes can also be electronically downloaded to other software applications for further processing, storage or transmission to other entities or other data processing systems.

Processing Medical Information Templates

Figure 6:
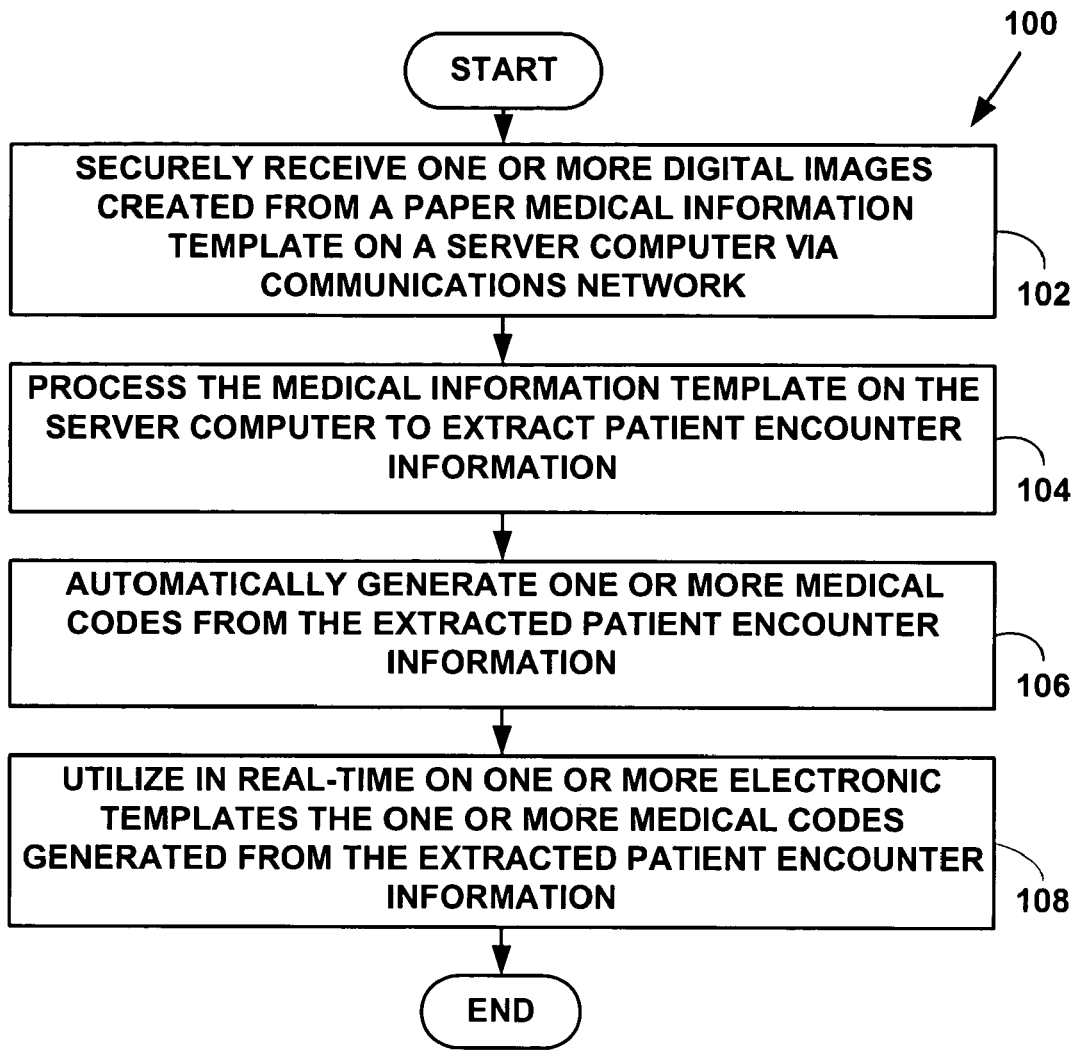
FIG. 6 is a flow diagram illustrating a method of processing medical information templates via the medical records system.

FIG. 6 is a flow diagram illustrating a Method 100 of processing medical information templates via the medical records system 10. At Step 102, one or more digital images created from a paper medical information template 12 are securely received on a server computer 20 via a communications network 24. The digital images of the medical information template were created by scanning a paper copy of the medical information template 12 into the medical records system 10 via the scanner 14. At Step 104, the one or more digital images are automatically processed on the server computer 20 to extract patient encounter information. At Step 106, one or more medical codes are automatically generated from the extracted patient encounter information. The one or more medical codes generated include, but are not limited to, one or more of E/M, CPT, HCPCS, ICD-9, ICD-10 or other types of codes. At Step 108, the one or more generated medical codes are generated from the extracted patient encounter information are utilized on one or more electronic templates. The one or more electronic templates are displayed on a graphical user interface (GUI) or the one or more electronic templates are used to produce additional medical information documents.

The one or more electronic templates can be displayed on a GUI in real-time directly after a patient encounter providing immediate access to the one or more electronic medical information templates created from the one or more generated medical codes.

The one or more generated medical codes can also be utilized via the one or more electronic templates to produce additional medical information documents, such as invoices, medical records, etc. The additional medical information documents can be produced via exemplary medical records system 10 or be sent to other data processing systems (not illustrated) for further processing. For example, the one or more electronic templates including the one or more generated medical codes (e.g., as XML or other types of electronic templates) can be sent electronically to another data processing system, such as a 3$^{rd}$ party or external medical billing system, that creates and sends an invoice to the patient after the patient encounter.

In such an embodiment, the one or more electronic templates may never be viewed or displayed, but treated as data that is processed automatically by other data processing systems. In such an embodiment, Method 100 is used to create electronic data that is used as an interface to other data processing systems.

The one or more electronic templates include, but are not limited to, an electronic invoice template, an electronic medical record template, a current compliant template, a nurse template, a review template, a diagnosis template; a provider template; and other types of electronic templates.

Chief Complaint Determines Selection of Specific History Template(s):

The chief complaint template describes an organization of an electronic medical record in such a way that medical information provided by personnel (including but not limited to the provider, nursing staff or even the patient himself or herself), can be documented using other electronic templates (e.g., a history template) or another paper template. For example, when a provider/or patient selects chief complaint, an additional electronic template (e.g., a history template) specific to that complaint is generated based on the chief complaint of the patient. This additional electronic template (specific to a given chief complaint) includes information that a medical provider generally documents or could generally be expected to document for a given chief complaint. This information may include, but is not limited to appropriate history of present illness ("HPI"), review of systems ("ROS"), past medical family social history ("PMSFH"), allergies, medications, vital signs, etc. This information may or may not be modified by or for the medical facility that collected the patient encounter information (e.g., via a review template).

Diagnosis determines selection of specific physical exam, treatment and disposition template(s): In addition, the organization of an electronic medical record can be presented in such a way that a paper or an electronic template for a healthcare provider for the majority of patients can be documented using another single electronic template (e.g., provider template). When a provider selects a diagnosis for a given patient, a specific electronic template is generated based on that diagnosis of patient (e.g., a diagnosis template). This specific electronic template (i.e., specific to the given diagnosis) includes information that the provider generally documents or could be expected to document for a given diagnosis. This information may include but not be limited to physical exam, treatments (including but not limited to medications, clinical procedures, dressings, splints, casts, crutches, changes in activity, or any other treatment), laboratory testing, diagnostic testing, referrals, consults, disposition, or any other items deemed relevant for the provider's documentation of this chart. A default set of the above data may or may not be set in advance, but can be modified by the provider. This information may or may not be modified by or for the medical facility that collected the patient encounter information (e.g., via a physician review template).

Method 100 may also further comprise generating an electronic invoice in real-time using the one or more medical codes calculated from the extracted patient encounter information. The electronic invoice includes a fee for the medical services provided during the patient encounter. The electronic invoice is presented in real-time via a graphical user interface ("GUI") (not illustrated in FIG. 6) or utilized in real-time via other data processing systems as was described above Method 100 may also further comprise generating an electronic medical record in real-time using the one or more medical codes calculated from the extracted patient encounter information and other information extracted from the patient encounter information. The electronic medical record is presented in real-time via a graphical user interface ("GUI") (not illustrated in FIG. 6) or utilized in real-time via other data processing systems as was described above.

The patient encounter information is extracted by processing the plural check-boxes or other electronically interpreted data and is stored in internal data structures with plural fields on the server computer 20. After Step 104, the internal data structure fields include an indication of which check-boxes and data fields were used (i.e., checked or filled out), and portions of the digital images corresponding to the original paper medical information template 12 may be placed into defined locations on a newly generated electronic invoice template, electronic medical record template, or other electronic template (e.g., nurse, insurance, etc.). The internal data structure fields also include links to the original digital images 54.

These internal data structure fields are also be used for (but are not limited to): (1) storing transcription of handwritten data (using handwriting recognition software, firmware or hardware) to replace the graphic image of handwritten data with transcribed text in the electronic medical record; (2) storing handwritten diagrams that are placed into an electronic template of an electronic medical record; (3) storing computerized text including generated medical codes, computerized text generated from check boxes and other information extracted from the patient encounter information that is displayed at various locations in one or more electronic templates such as the electronic invoice electronic medical record, etc.; (4) storing transcriptions of audio dictation data with transcribed text included in the electronic medical record via audio dictation interface 27.

For example, when the paper medical information template 12 is used to document a patient encounter, a provider can mark the encounter as needing dictation. The electronic medical record created is marked with a status of "dictation pending." The electronic medical record generated is pre-populated for the pending dictation text including information from the patient encounter. When the provider has time, he/she securely logs into the audio dictation interface 27 (e.g., via a secure web-site) on the medical records system 10 views a queue of patient charts awaiting dictation. A dictation voice file is captured from the provider via the dictation interface and is directly associated with the electronic medical record. A medical transcriptionist later securely logs onto the same dictation interface, listens to the dictation file and generates an electronic transcript from the dictation. The medical record is populated with electronic information from the electronic transcript. Thus, the electronic medical records can also be dynamically populated with provider dictation text based on the result of the patient encounter.

One set of patient encounter information extracted from the one or more digital images of the paper medical information template 12 at Step 104 (and Step 114 described below) includes extracting historical information ("HX") obtained from the patient encounter and populating internal data structures. In one embodiment of the invention, extracted historical information is compared against predetermined values for an HX matrix (described below) for determining a historical value used to calculate a medical code. However, the invention is not limited to this embodiment and the extracted historical information can be used with other internal data structures to generate a medical code.

The HX information includes, but is not limited to, pre-defined elements that make up chief complaint ("CC") information, history of present illness ("HPI") information, past medical, family, social history information ("PFMSH") and review of system ("ROS") information.

Table 1 illustrates exemplary HX information collected. However, the present invention is not limited to this HX information, more, less and other types of HX information can also be collected from the patient encounter information.

TABLE 1

HX Information

Chief Complaint (CC):

Description of one or more problems (e.g., sore throat, chest pains, trouble breathing, etc.)
History of Present Illness (HPI):

Location; quality; severity; duration; timing; context; modifying factors; associated signs and symptoms.
Past medical, family, social history (PFMSH):

Medical History—the patient's past experiences with illnesses, operations, injuries and treatments.
Family History—a review of medical events in the patient's family, including diseases which may be hereditary or place the patient at risk.
Social History—an age appropriate review of past and current activities.
Review of Systems (ROS):

Constitutional; eyes, ears, nose, mouth, throat; cardio-vascular; respiratory; GI; GU; muscular; neurological; psychological; immune; etc.

Another set of patient encounter information extracted from the digital images of the paper medical information at Step 104 and 114 includes extracting physical examination information ("PX") obtained from the patient encounter and populating internal data structures. In one embodiment of the invention, extracted physical examination information is compared against predetermined values for a PX matrix (described below) for determining a physical examination value used to calculate a medical code. However, the invention is not limited to this embodiment and the extracted physical examination information can be used with other internal data structures generate a medical code.

Table 2 illustrates where body areas and organ systems from which PX information is collected. However, the present invention is not limited to this PX information, more, less and other types of PX information can also be collected from the patient encounter information.

TABLE 2

PX Areas

Body Areas:

Head, including face; Back including spine; Chest including breasts; Genitalia including groin and buttocks; Abdomen; Neck; Extremities; etc.
Organ Systems:

Constitutional; eyes, ears, nose, mouth, throat; cardio-vascular; respiratory; GI; GU; muscular; neurological; psychological; immune; etc.

Table 3 illustrates possible levels of the physical exam types of PX information determined. This example uses one specific set of guidelines commonly referred to and published by the Centers for Medicare & Medicaid Services ("CMS") as the 1997 Documentation Guidelines for Evaluation and Management Services, but can utilize other methods or guidelines as determined by the type of exam or by changes in prescribed or allowable guidelines. In addition, the PX information is exemplary only, and the present invention is not limited to such PX information.

The PX information is determined in part from processing the check-boxes completed in the medical diagnosis box 41 illustrated in FIG. 2B on the paper medical information template 12 and in FIG. 3.

TABLE 3

PX Types

| | |
|---|---|
| PF | One to five elements identified by a bullet (e.g., one to five body areas or organs) |
| EXPF | At least six elements identified by a bullet (e.g., up to a total of six organ systems) |
| DET | At least twelve items identified by a bullet from 2 (or more) PX areas |
| COMP | Two or more elements identified by a bullet in nine or more organ systems. |

The PX types include, but are not limited to: a problem focused ("PF") exam that includes 1-5 specific exam elements identified by a bullet on the paper medical information template 12; an expanded problem focused exam ("EXPF") that includes at least 6 specific exam elements; identified by a bullet, Detailed exam ("DET") that includes at least 12 elements in two or more areas/systems, identified by a bullet; and a comprehensive exam ("COMP") that includes documentation of at least two elements from each of nine areas/systems identified by a bullet.

Another set of patient encounter information extracted from the digital image of the paper medical information at Steps 104 and 114 includes extracting complexity of medical decision making information ("CX") obtained from the patient encounter and populating internal data structures. In one embodiment of the invention, extracted complexity information is compared against predetermined values for a CX matrix (described below) for determining a complexity value used to calculate a medical code. However, the invention is not limited to this embodiment and the extracted complexity information can be used with other internal data structures generate a medical code. The CX information includes a number of diagnosis ("DX") or treatment options and risk ("RISK") information.

The DX information includes, but is not limited to: straight forward ("SF") diagnosis; a low number of diagnoses ("LOW") a moderate number of diagnoses ("MOD"); and a high number of possible diagnoses ("HIGH") This DX scoring can be performed using an objective scoring system as outlined in Appendix B. A unique aspect of this invention includes (but is not limited to) presentation of these choices in check-box form with each of a maximum number of choices in each category represented by a check-box. Scoring of the DX section can then be performed by adding a point value of each box to obtain the total score in the DX section. Although, scoring of the DX section is not limited to this method, if it is used the following scores correlate with the various levels of DX: ($\leq 1$) minimal; (2) limited; (3) multiple; or (4) extensive.

The RISK information includes: minimal or straight forward ("SF") risk in which the medical problem is self-limited or a minor problem (e.g., cold, insect bite, etc.); low risk ("LOW") in which the medical problem includes two or more minor problems, one stable chronic illness (e.g., well controlled hypertension or non-insulin dependent diabetes, cataract, etc.) or an acute uncomplicated illness or injury (allergic reaction, simple sprain); moderate risk ("MOD") in which the medical problem includes one or more chronic illnesses with mild exacerbation, progression, or side effect treatment, two or more stable chronic illnesses, an undiagnosed new problem with uncertain prognosis (e.g., lump in breast or prostrate, etc.) an acute illness with systemic symptoms (e.g., pneumonitis, colitis, etc.) or an acute complicated injury (e.g., head injury with brief loss of consciousness); and high risk ("HIGH") in which the medical problem includes one or more chronic illnesses with severe exacerbation, progression or side effects of treatment, or acute or chronic illnesses or injuries that may pose a threat to life or bodily function (e.g., multiple trauma, acute MI, pulmonary embolus, severe respiratory distress, progressive severe rheumatoid arthritis, psychiatric illness with potential threat to self or others, acute renal failure, etc.) or an abrupt change in neurological status (e.g., seizure, TIA, weakness or sensory loss, etc.).

In one embodiment of the invention, omission of analysis of an amount and/or complexity of data reviewed is completed Omission of this aspect of a CX matrix can alter a CX score of very few patient encounters, if the previously used scoring for DX and RISK are utilized. Scoring of an amount and/or complexity of data reviewed may be added to the medical records processing system 10 if indicated by physician utilization, patient population, or changes in coding guidelines.

Another set of patient encounter information extracted from the digital image of the paper medical information at Steps 104 and 114 includes extracting patient status information and patient demographic information. The patient status information includes, but is not limited to, new patient, existing patient, consult, pre-surgery, hospital, etc. The patient demographic information, includes, but is not limited to, patient date-of-birth, etc.

The patient status information and patient demographic information is used in certain situations to override or modify the one or more medical code automatically generated at Steps 106 (and Step 118 described below) and/or to generate additional medical codes. For example, the patient status information, such as admit to the hospital can automatically override or generate addition types of medical codes. As another example, the patient demographic information such as date-of-birth within a certain pre-determined range (e.g. very young or very old) can automatically override or generates other types of medical codes.

Another set of patient encounter information extracted from the digital image of the paper medical information at Steps 104 and 114 includes extracting medical diagnosis information for the problems described during the patient encounter.

Another set of patient encounter information extracted from the digital image of the paper medical information at Steps 104 and 114 includes extracting clinical procedure information, treatment information and supply information. The clinical procedure information, includes, but is not limited to, clinical or hospital or surgical procedure information, such as stitches, applying cast, a desired operation, diagnostic tests (e.g., x-rays, MRI scans, CRT scans, etc.) and other types of clinical procedure information. The treatment information, includes, but is not limited to, medications, physical therapy, etc. The supply information includes, but is not limited to, types of medical supplies used on the patient such as bandages, casts, crutches, etc.

However, the present invention is not limited to extracting the patient encounter information described and other types of patient encounter information can also be extracted.

One type of medical codes automatically generated at Step 106 (and Step 118 described below) includes CPT E/M codes for new outpatient visits. Table 4 illustrates a few exemplary such medical codes and their corresponding requirements. The codes in Table 4 illustrate only a selected few of the many AMA CPT E/M codes and the present invention is not limited to generating these exemplary medical codes.

TABLE 4

New Outpatient: CPT Code 99201
HX: EXPF
PX: EXPF
CX: SF
Provider Time: 10 minutes
New Outpatient: CPT Code 99202
HX: EXPF
PX: EXPF
CX: SF
Provider Time: 20 minutes
New Outpatient: CPT Code 99203
HX: DET
PX: DET
CX: LOW
Provider Time: 30 minutes
New Outpatient: CPT Code 99204
HX: COMP
PX: COMP
CX: MOD
Provider Time: 45 minutes
New Outpatient: CPT Code 99205
HX: COMP
PX: COMP
CX: HIGH
Provider Time: 60 minutes Another type of medical code generated at Step 106 and 118 includes AMA CPT codes for established outpatient visits. Table 5 illustrates such exemplary codes and their corresponding requirements. The codes in Table 5 illustrate only a selected few of the many CPT E/M codes and the present invention is not limited to generating these exemplary medical codes.

TABLE 5

Established Outpatient: CPT Code 99212
HX: PF
PX: PF
CX: SF
Provider Time: 10 minutes
Established Outpatient: CPT Code 99213
HX: EXPF
PX: EXPF
CX: LOW
Provider Time: 15 minutes
Established Outpatient: CPT Code 99214
HX: DET
PX: DET
CX: MOD
Provider Time: 25 minutes
Established Outpatient: CPT Code 99215
HX: COMP
PX: COMP
CX: HIGH
Provider Time: 40 minutes According to current AMA CPT guidelines, time is only to be used to determine the level of E/M code if greater than 50% of the face-to-face time of the encounter involved counseling or coordination of care. If applicable coding guidelines are revised at some future date, then time may be factored as indicated by these changes.

Step 106 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

Figure 7:
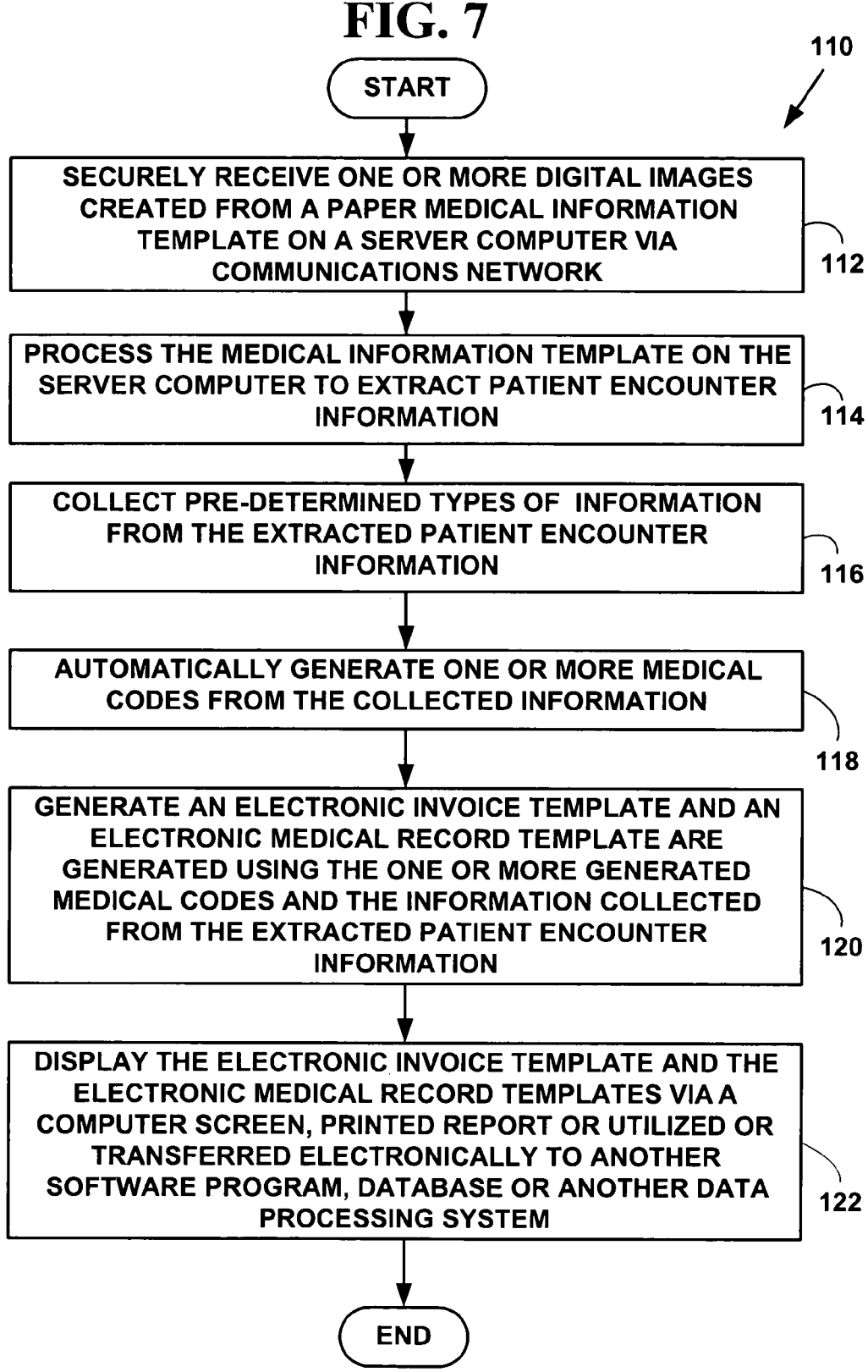
FIG. 7 is flow diagram illustrating a method of processing medical information templates via the medical records system.

FIG. 7 is a Method 110 for automatically calculating a medical code from patient encounter. At Step 112, one or more digital images created from a paper medical information template 12 are securely received on a server computer 20 via a communications network 24. The digital images of the medical information template were created by scanning a paper copy of the medical information template 12 into the medical records system 10 via the scanner 14. At Step 114, the one or more digital images are automatically processed on the server computer 20 to extract patient encounter information. At Step 116, historical information, physical examination information, complexity information, diagnosis, clinical procedures, tests, supplies and other data are collected from the extracted patient encounter information. At Step 118, one or more medical codes are automatically generated from the information collected from the extracted patient encounter information. The one or more medical codes generated include, but are not limited to, one or more of E/M, CPT, HCPCS, ICD-9 ICD-10, or other medical codes. At Step 120, an electronic invoice template and an electronic medical record template are automatically generated in real-time using the one or more generated medical codes collected from the extracted patient encounter information. At Step 122, the electronic invoice template and the electronic medical record templates are displayed in real-time via a computer screen, printed report or utilized or transferred electronically to another software program, database or another data processing system.

Step 118 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

Figure 8:
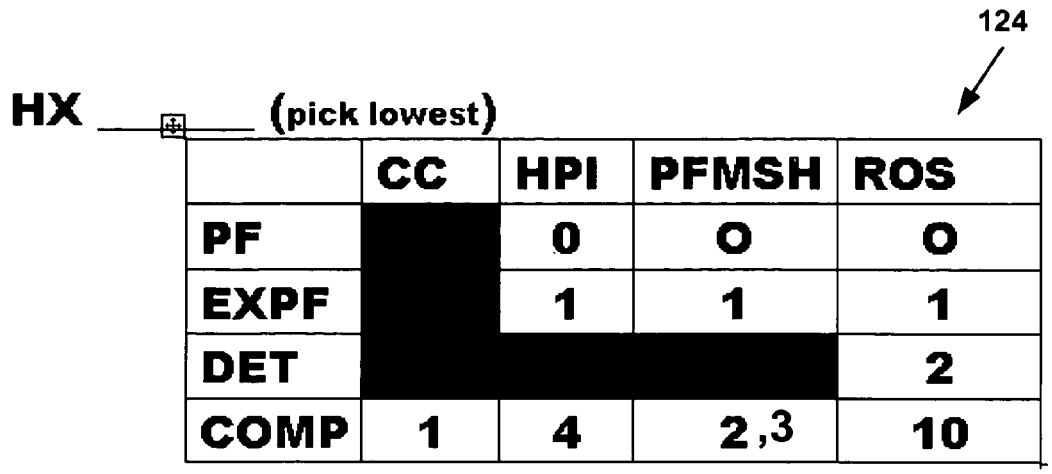
FIG. 8 is a block diagram illustrating an exemplary HX matrix.

FIG. 8 is a block diagram illustrating an exemplary HX matrix 124. The HX matrix 124 is used to determine a history value from the historical information extracted from the patient encounter and used is to generate the medical codes. The HX matrix includes fields for the CC, HPI, PFMSH and ROS elements as described above.

Figure 9:
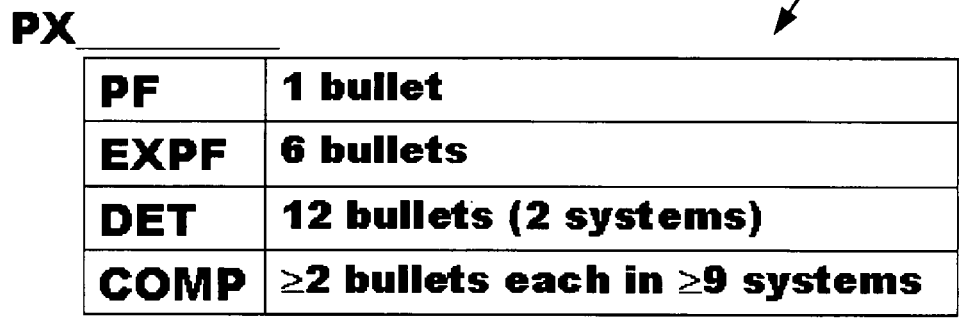
FIG. 9 is a block diagram illustrating an exemplary PX matrix.

FIG. 9 is a block diagram illustrating an exemplary PX matrix 126. The PX matrix 126 is used to determine a physical examination value from the physical examination extracted from the patient encounter and is used to generate the medical codes. The PX matrix includes fields for the PF, EXPF, DET and COMP elements as described above and a count of the check-boxes extracted as described in Table 3 above.

Figure 10:
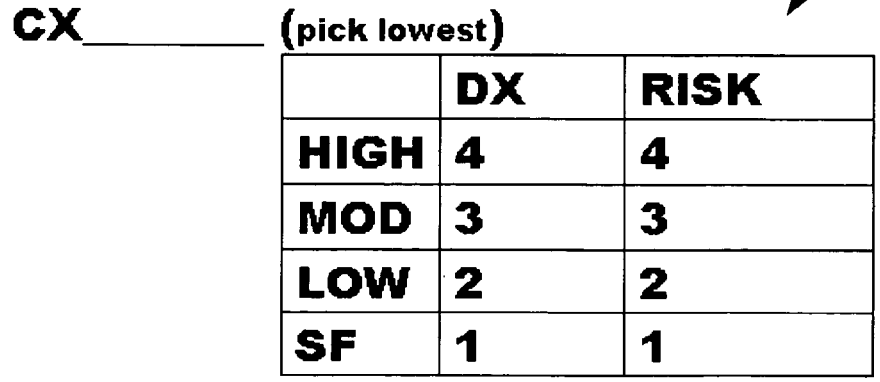
FIG. 10 is a block diagram illustrating an exemplary CX matrix.

FIG. 10 is a block diagram illustrating an exemplary CX matrix 128. The CX matrix 128 is used to determine a complexity value from the complexity information extracted from the patient encounter and is used to generate the medical codes. The CX matrix includes fields for DX and RISK and the SF, LOW, MOD and HIGH elements as described above.

FIG. 11 is a block diagram illustrating an exemplary final E/M matrix 130 for a new outpatient. The final E/M matrix 130 is used to calculate a medical code with the historical value, the physical examination value and the complexity value determined from the HX 124, the PX 126 and the CX 128 matrices. The final E/M matrix 130 includes possible values determined from the HX, PX and CX matrices. It also includes a set of medical codes that can be calculated. FIG. 11 illustrates a set of CPT E/M codes, 99201 through 99205 as illustrated in Table 4. FIG. 11 is exemplary only and the invention is not limited to this E/M matrix. The invention includes other plural matrices to generate other types of medical codes.

FIG. 12 is a block diagram illustrating an exemplary final E/M matrix 132 for an established outpatient. The final E/M matrix 132 also includes values determined from the HX, PX and CX matrices. It also includes a set of medical codes that can be calculated. FIG. 12 illustrates a set of CPT E/M codes, 99212 through 99215 as illustrated in Table 5. In this example, only two of the three aspects of the HX, PX, and CX need meet the level for the final code. FIG. 12 is exemplary only and the invention is not limited to this E/M matrix. The invention includes plural other matrices to generate other types of medical codes.

Method 110 is illustrated with an exemplary simple patient encounter. An 18-year female patient arrives at a family practice office as a new patient complaining of an acute bee sting on her right fifth finger. She indicates that she has no chronic medical problems, is using no medications and is not known to have a severe allergy to bee stings. She has only minor swelling and no other symptoms. The provider records the patient history on paper medical information template 34, and the provider checks a only small number of check-boxes for the physical exam, template 40 and a minor, new problem in box 41 of FIG. 2B. The patient encounter information is processed with Steps 112, 114 and 116 of Method 110.

At Step 116, referring to FIG. 8, a history value is determined from the HX matrix 124 using the historical information collected from the patient encounter and stored in the internal data structures. Since the chief complaint ("CC") is a bee sting, the history of the present illness ("HPI") is brief, the medical history is collected (i.e., not allergic to bee strings, no chronic medical problems, on no medications, etc.) and the review of systems ("ROS") is limited to constitutional and respiratory systems, the history value returned from the HX matrix is EXPF for a "extended problem focused" complaint.

At Step 116, referring to FIG. 9, a physical examination value is determined from the PX matrix 126 using the physical examination information collected from the patient encounter. The physical exam could be a PF value.

At Step 116, Referring to FIG. 10, a complexity value is determined from the CX matrix 128 using the complexity information collected from the patient encounter. Since a local bee sting reaction is a minor, self-limited problem, DX value is one. The patient may be given over-the-counter medications so the RISK score is two. This makes the complexity value ("CX") a straight forward, or SF value.

At Step 118, referring to FIG. 11, a medical code is generating from the final E/M matrix 130 for a new outpatient using the history value of EXPF from the HX matrix 124, the physical examination value of PF from the PX matrix 126, and the complexity value of SF from the CX matrix 128. The medical code generated is 99201.

Method 110 is illustrated with a second more complex exemplary patient encounter. A 58-year male established patient arrives at a family practice physician office complaining of acute onset of one hour of 10/10 chest pain, accompanied by shortness of breath. The patient suffers from chronic diabetes, has had his left leg amputated and has advanced heart disease, lung disease and kidney disease. There is a history of diabetes in his family and he is currently a heavy smoker of cigarettes. The provider records the patient encounter on paper medical information template 30 for which the provider checks a large number of check boxes and fills in a large number of blanks for the patient encounter including multiple check-boxes in box 41 of FIG. 2B.

At Step 116, referring to again FIG. 8, a history value is determined from the HX matrix 124 using the historical information collected from the patient encounter. Since the chief complaint ("CC") is pain; the history of the present illness ("HPI") is extended including four or more elements (location, chest; associated symptoms, shortness of breath; duration, one hour; severity 10/10); the past family, medical and social history is relevant and includes elements of both the medical and social history. (e.g., leg amputation, pain in fingers and kidney disease related to diabetes, heart and lung disease related to heavy smoking, older male) and the review of systems ("ROS") includes multiple ($\geq 10$) systems (e.g., constitutional, neurological, cardio-vascular, respiratory, etc.), the history value returned from the HX matrix is COMP for a comprehensive history.

At Step 116, referring again to FIG. 9, a physical examination value is determined from the PX matrix 126 using the physical examination information collected from the patient encounter. All elements identified by a bullet in over 9 areas/systems are documented in FIG. 2B so a COMP value (comprehensive exam) is generated.

At Step 116, referring again to FIG. 10, a complexity of medical decision making value is determined from the CX matrix 128 using the complexity information collected from the patient encounter. Since the problems are new and additional workup is planned, the detailed exam ("DX") value is four. Since the risk of morbidity or mortality is high based on the life-threatening nature of the patient's presentation, chief complaint the RISK value is also four. This makes the complexity of medical decision making value a HIGH value.

At Step 118, referring to FIG. 12, a medical code is generated from the final E/M matrix 132 for an established outpatient using the history value of COMP from the HX matrix 124, the physical examination value of COMP from the PX matrix 126, and the complexity of medical decision making value of HIGH from the CX matrix 128. The medical code generated is 99215. (See also Table 5).

Figure 2C:
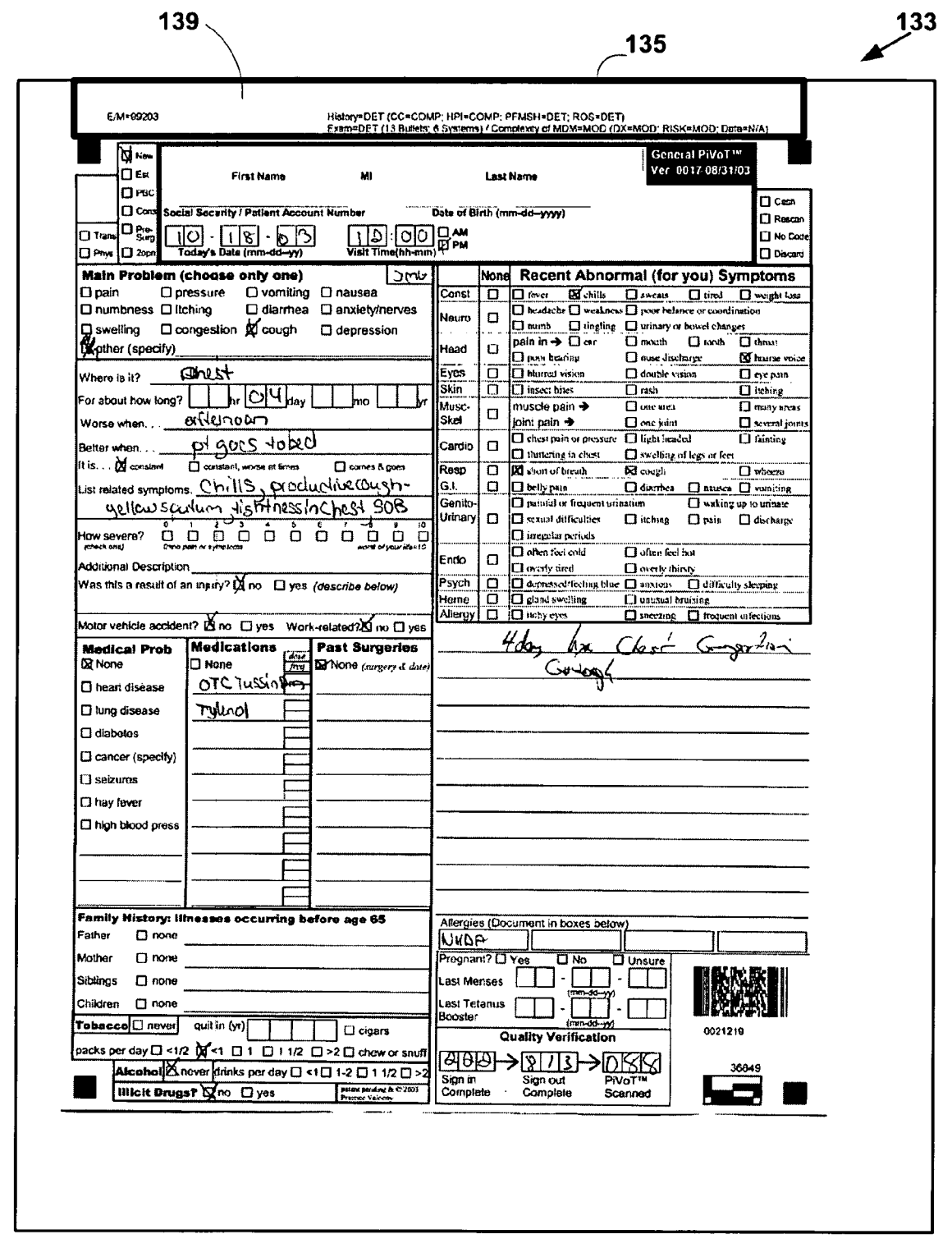
Figure 2D:
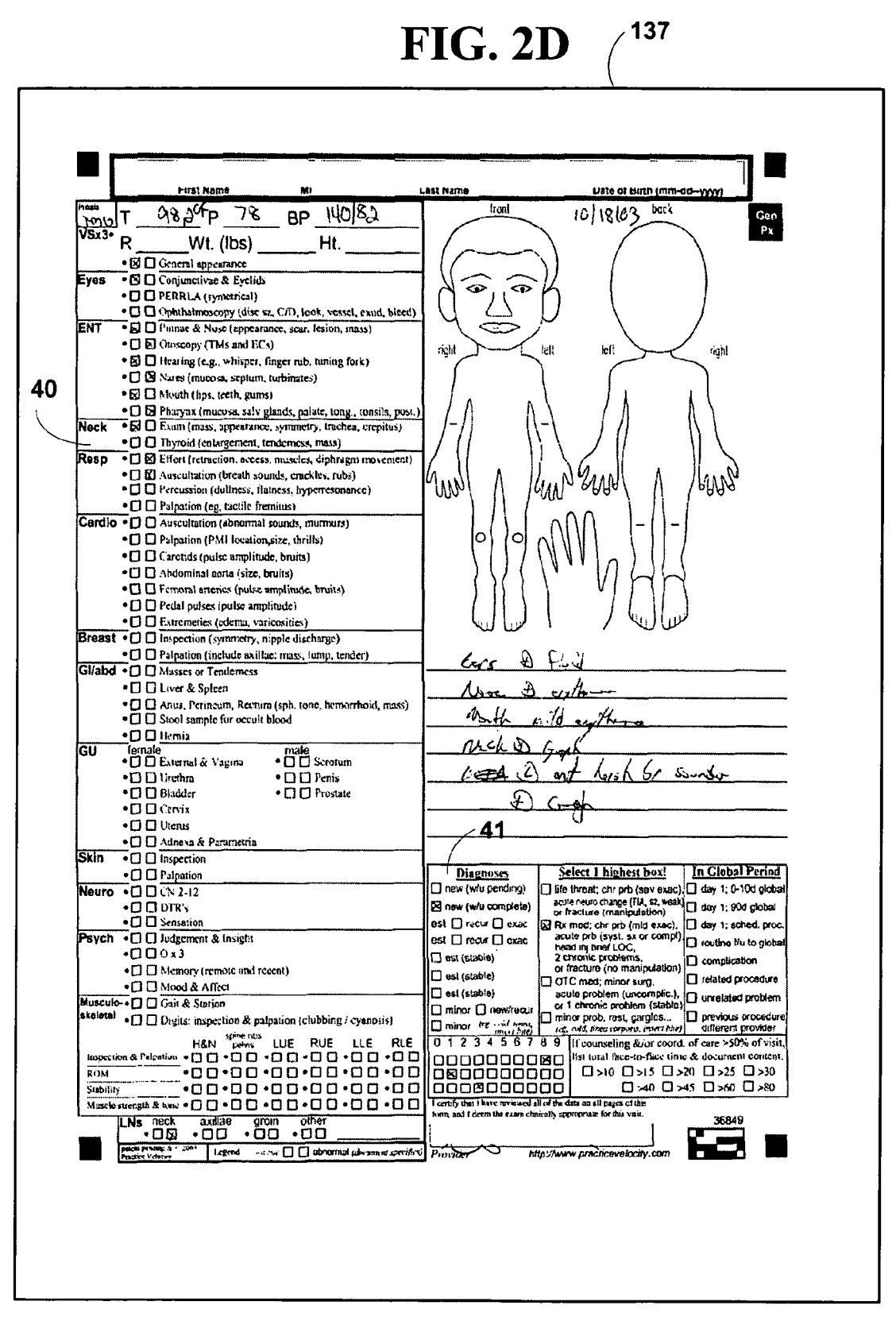

FIGS. 2C and 2D are a block diagram 133 illustrating a front side 135 and a back side 137 of another exemplary paper medical information form that further illustrates an exemplary coding summary 139 produced from exemplary patient encounter information.

The patient encounter illustrated in FIGS. 2C and 2D is fictitious and not the result of a real patient encounter. Thus, this fictitious medical data does not violate the privacy of any real individual under HIPPA or other federal or state laws.

This fictitious patient, a new outpatient, complained of a cough, chills, and tightness in the chest. During the patient encounter various boxes on the paper information template were checked off including a check of the patient's neck (box 40 FIG. 2D and normal green box 44 illustrated in FIG. 3). A diagnosis was also made in the Diagnoses box (new w/u complete box 41 FIG. 2D and FIG. 3) and the provider included handwritten notes. The provider spent about 30 with the patient.

The exemplary coding summary 139 is attached to the one or more digital images after the one or more medical codes are generated. The exemplary coding summary 139 is also illustrated in Table 6.

TABLE 6

CODING SUMMARY OUTPUT FROM PROCESSING OF
EXEMPLARY PAPER MEDICAL INFORMATION FORM
ILLUSTRATED IN FIGS. 2C and 2D E/M=99203
History=DET (CC=COMP: HPI=COMP; PFMSH=DET; ROS=DET)
Exam=DET (13 Bullets; 6 Systems)/Complexity of MDM=MOD (DX=
MOD; RISK=MOD; Data=N/A)

As FIGS. 2C and 2D and Table 6 illustrate, an exemplary E/M code generated from this fictitious patient encounter was 99203 for a new outpatient (Table 5 and FIG. 11). The exemplary E/M code of 99203 is generated with the methods described herein.

Figure 13:
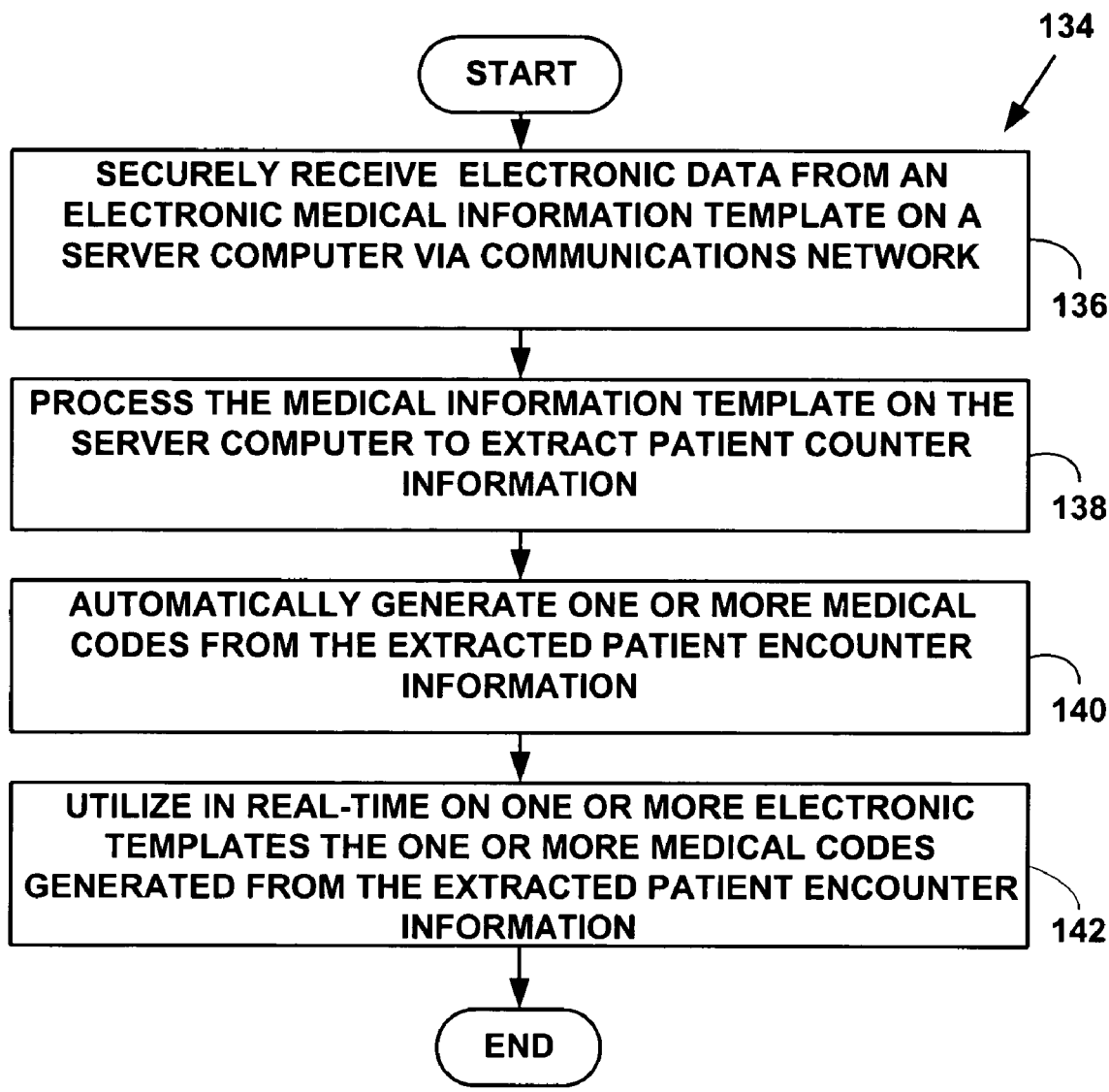
FIG. 13 is a flow diagram illustrating a method of processing medical information templates via the medical records system.

FIG. 13 is a flow diagram illustrating a Method 134 of processing medical information templates via a medical records system. At Step 136, electronic data created from an electronic medical information template 12' is securely received on a server computer 20 via a communications network 24. The electronic data was created on a client electronic device 18 using an electronic medical information template 12'. At Step 138, the electronic data is automatically processed on the server computer 20 to extract patient encounter information. At Step 140, one or more medical codes are automatically generated from the extracted patient encounter information. The one or more medical codes generated include, but are not limited to, one or more of E/M, CPT, HCPCS, ICD-9, ICD-10, or other types of codes. At Step 142, the one or more medical codes generated from the extracted patient encounter information are presented on one or more electronic templates that are displayed on a graphical user interface (GUI) or the one or more electronic templates are utilized to produce additional medical information documents. The one or more electronic templates include, but are not limited to, an electronic invoice template, an electronic medical record template, a current compliant template, a nurse template, a review template, a diagnosis template; a provider template; and other types of electronic templates.

electronically to another software program, database or another data processing system.

Method 134 is used to process digital data extracted patient encounter information entered on a client electronic device 18 using an electronic medical information template 12' instead of a paper medical information template. Method 134 processes such electronic data in a manner similar to the digital images described for Methods 100 and 110.

Figure 14:
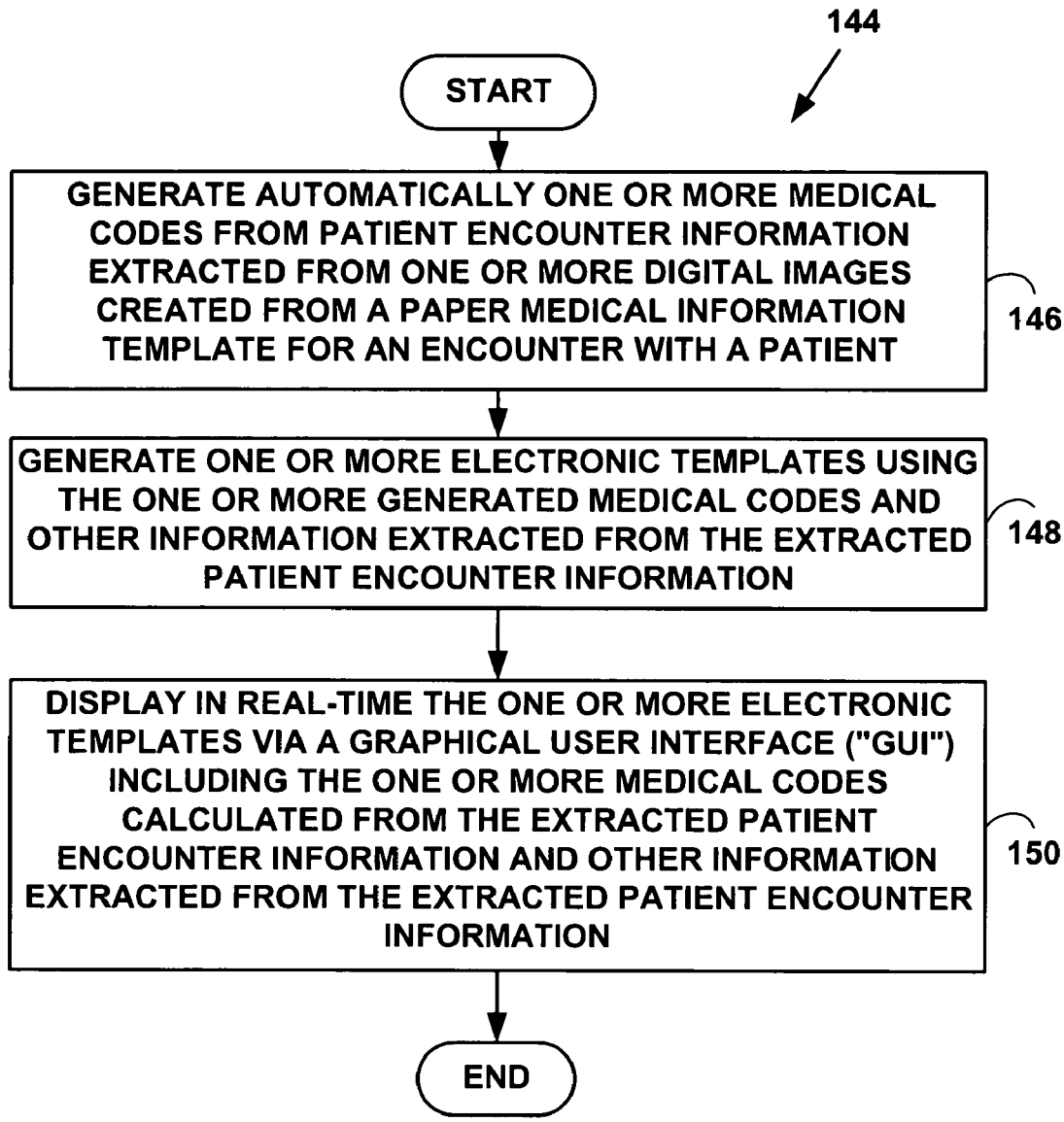
FIG. 14 is a flow diagram illustrating a method of processing medical information templates via the medical records system.

FIG. 14 is a flow diagram illustrating a Method 144 of processing medical information templates via the medical records system. At Step 146, one or more medical codes are generated automatically from patient encounter information extracted from one or more digital images created from a paper medical information template 12 for an encounter with a patient. The one or more medical codes generated include, but are not limited to, one or more of E/M, CPT, HCPCS, ICD-9, ICD-10, or other medical codes. At Step 148, one or more electronic templates are generated automatically using the one or more generated medical codes and other information extracted from the extracted patient encounter information. The one or more electronic templates include, but are not limited to, an electronic invoice template, an electronic medical record template, a current compliant template, a nurse template, a review template, a diagnosis template; a provider template; and other types of electronic templates. At Step 150, the one or more electronic templates that are displayed on a graphical user interface (GUI) or the one or more electronic templates that are utilized to produce additional medical information documents including the one or more medical codes generated from the extracted patient encounter information and other information extracted from the extracted patient encounter information.

Step 146 further includes creating a coding summary of the one or more medical codes generated from the extracted patient encounter information. The created coding summary is attached to the one or more digital images. The coding summary is used to verify that the proper medical codes were generated from the extracted patient encounter information and can be used by auditors to verify the proper medical codes were generated.

The methods and systems described herein were illustrated with respect to a patient examination view or perspective. However, the invention is not limited to this view or perspective. The methods and system described herein are also used to provide automated processing and real-time collection and display of other types of medical information associated with, or generated by a patient encounter to provide 360° view of an individual patient after a patient encounter. The methods and system are used to process, display and/or utilize in real-time all available information for a patient immediately after a patient encounter.

Although description of this method has been limited to the outpatient encounter, this same methodology may be applied to documentation and coding of in-hospital encounters, consults, preventative examinations and other types of patient encounters.

Figure 15:
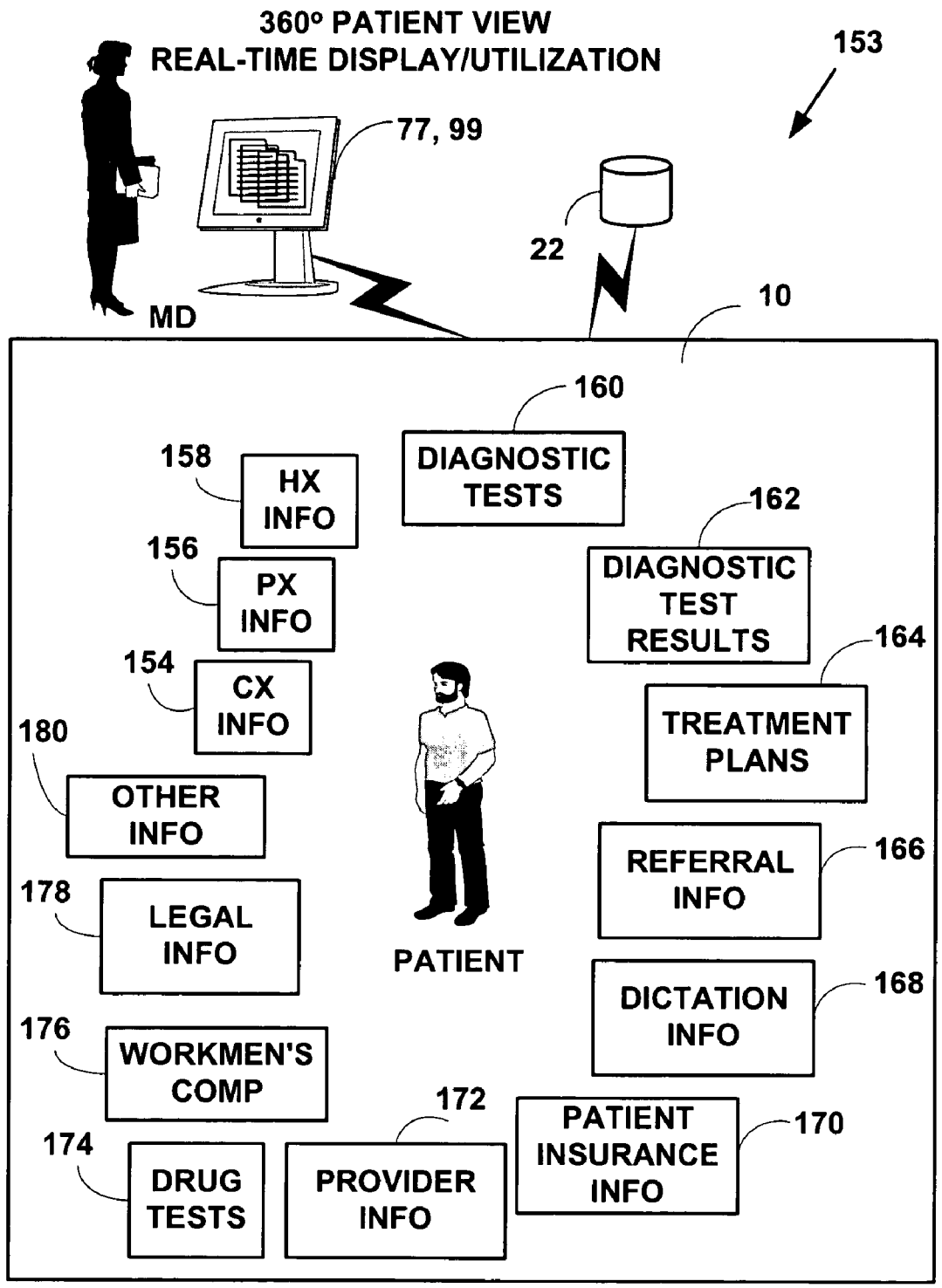
FIG. 15 is a block diagram illustrating a 360° real-time view of a patient encounter.

FIG. 15 is a block diagram illustrating a 360° real-time view 152 of a patient encounter. The 360° real-time view includes, but not limited to, HX 154, PX 156, CX 158 information extracted, diagnostic procedures ordered 160 (e.g., blood tests, x-rays, MRI scans, CT scans, etc.); diagnostic procedures results 162; treatment plans 164; referral information 166; dictation information 168; patient insurance information 170; provider information 172; and information such drug testing information 174, workmen's comp information 176, legal information 178, and other types of information 180 associated with a patient and/or a patient encounter.

The method and system help reduce the complexity of collecting patient encounter information and allow easy collection, processing and recording of medical information codes such as diagnosis codes, billing codes, insurance codes, etc.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more fewer or equivalent elements may be used in the block diagrams.

The claims should not be read as limited to the described order or elements unless stated to that effect. In addition, use of the term "means" in any claim is intended to invoke 35 U.S.C. §112, paragraph 6, and any claim without the word "means" is not so intended. Therefore, all embodiments that come within the scope and spirit of the following claims and equivalents thereto are claimed as the invention.

We claim:

1. A method of processing medical records, comprising:
   (a) creating on a network device with one or more processors and one or more associated databases, one or more different medical templates capable of being used to enter information from an encounter with a patient, wherein the one more medical templates comprise a plurality of data fields comprising:
(i) patient history data;
(ii) patient physical condition data;
(iii) summary information;
(iv) existing patient history information; and
(v) complexity risk coding information;
(b) printing the one or more different medical templates on paper forms;
(c) entering patient encounter information from a patent encounter into the plurality of data fields by writing on the paper forms with a writing utensil, thereby creating completed paper forms;
(d) scanning the completed paper forms into the network device;
(e) digitizing the completed paper forms by:
(i) identifying from the network device a plurality of locations of data fields on the completed paper forms; and
(ii) performing optical character recognition on the network device on data created with the writing utensil at each of the plurality of identified locations of the data fields;
(f) aggregating the recognized data into an electronic patient medical record and storing the electronic patient medical record on the network device; and
(g) determining on the network device with the stored electronic patient medical record for the patient encounter represented by the paper forms:
(i) medical and billing codes;
(ii) legal compliance for medical treatment provided to the patient during the patient encounter;
(iii) an appropriateness of care based on the stored patient data and the medical treatment provided during the patient encounter;
(iv) a physician practice profile by aggregating data for a particular physician; and
(v) data for use in research studies.

2. The method of claim 1 further comprising:
generating a plurality of electronic medical templates in real-time using the determined medical and billing codes; and
utilizing in real-time the generated plurality of electronic medical templates and the stored electronic medical record by displaying the generated plurality of electronic medical templates and the stored electronic medical record on a graphical user interface (GUI) on the network device.

3. The method of claim 2 wherein the one or more generated electronic templates include one or more of an electronic invoice template, and electronic medical record template, a chief compliant template, a diagnosis template, a nurse template, a review template, or provider template.

4. The method of claim 2 wherein the generating step includes:
creating a coding summary of the one or more medical and billing codes generated from the stored electronic patient medical record; and
attaching the created coding summary to the stored electronic patient medical record, wherein the coding summary can be used to verify that the proper medical codes where generated from the patient.

5. The method of claim 2 further comprising:
selecting a generated electronic medical information template on the network device;
generating automatically one or more additional electronic medical information templates based on the selected generated electronic medical information template and the stored electronic medical record, wherein the one or more additional electronic information templates including additional electronic medical information templates for medical personnel, the patient or a healthcare provider.

6. The method of claim 1 wherein the one or more printed paper forms include a limited number of check-boxes specifically selected for a specific type of medical practice, wherein the limited number of check boxes reduce a risk associated with making a complex medical decision by allowing only a single check box for each level of risk, wherein digitizing the plurality of check-boxes generates an appropriate number and type of medical and billing codes for the specific type of medical practice including complexity risk coding information for the specific type of medical practice.

7. The method of claim 6 wherein digitizing the plurality of check-boxes includes generating: a plurality of HX data fields including patient history information; a plurality of PX data fields including patient physical condition information; a plurality of CX data fields including complexity risk information; and one or more E/M data fields including evaluation and management codes, wherein the generated one or more E/M data fields include summary information obtained by aggregating information from the HX, PX and CX data fields.

8. The method of claim 1 further comprising a computer readable medium having stored therein instructions for causing one or more processors to execute the steps of the method.

9. The method of claim 1 wherein the determined medical and billing codes include one or more of Evaluation and Management codes ("E/Ms") codes, Current Procedural Terminology ("CPTs") codes, Health Care Financing Administration Common Procedural Coding System ("HCPCS") codes, International Classification of Diseases $9^{th}$ Edition Clinical Modification ("ICD-9") codes or International Classification of Diseases $10^{th}$ Edition Clinical Modification ("ICD-10") codes.

10. The method of claim 1 wherein determining step includes:
determining historical information, physical examination information, complexity information, patient status information, patient demographic information, diagnosis information, clinical procedure information and supply information from the stored electronic medical record on the network device.

11. The method of claim 1 further comprising:
generating automatically one or more medical and billing codes using historical, physical complexity of medical decision making information, patient status information, patient demographic information, diagnosis information, clinical procedure information, treatment information and supply information collected from the stored patient medical record.

12. The method of claim 1 further comprising verifying in real-time the stored patient medical record via the scanned completed paper forms.

13. The method of claim 1 wherein the determined medical and billing codes include one or more medical codes specifically generated for a new patient or one or more medical codes specifically generated for an existing patient.

14. The method of claim 1 wherein complexity risk coding information helps eliminate an amount and complexity of patient data to be collected and a number of diagnostic options to be considered during the patient encounter thereby reducing a risk associated with making a complex medical decision and limiting an amount and complexity of patient data to be processed and reviewed.

15. A system for processing medical records on a plurality of network devices each with one or more processors, comprising in combination:

a first network device for:
  creating one or more different medical templates capable of being used to enter patient encounter information, wherein the one or more medical templates comprises a plurality of data fields comprising:
    (i) patient history data;
    (ii) patient physical condition data;
    (iii) summary information;
    (iv) existing patient history information;
    (v) complexity risk coding information;
  printing on the first network device the one or more different medical templates on paper forms;
  entering patient encounter information from a patent encounter into the plurality of data fields by writing on the paper forms with a writing utensil, thereby creating completed paper forms;

a second network device with one or more associated databases for:
  scanning the completed paper forms;
  digitizing the completed paper forms by:
    (i) identifying from the network device a plurality of locations of data fields on the completed paper forms;
    (ii) performing optical character recognition on the second network device on data created with the writing utensil at each of the plurality of identified locations of the data fields;
  aggregating the recognized data into an electronic patient medical record and storing the electronic patient medical record on the second network device;
  determining on the second network device with the stored electronic patient medical record for the patient encounter represented by the paper forms:
    (i) medical and billing codes;
    (ii) legal compliance for medical treatment provided to the patient during the patient encounter;
    (iii) an appropriateness of care based on the stored patient data and the medical treatment provided during the patient encounter;
    (iv) a physician practice profile by aggregating data for a particular physician; and
    (v) data for use in research studies;
  generating one or more electronic templates from the stored electronic medical record on the second network device; and
  displaying the scanned paper forms, the stored electronic medical record and the generated one or more electronic templates on a graphical user interface (GUI) on the second network device.

16. The system of claim 15 wherein the determined medical and billing codes include one or more of Evaluation and Management codes ("E/Ms") codes, Current Procedural Terminology ("CPTs") codes, Health Care Financing Administration Common Procedural Coding System ("HCPCS") codes International Classification of Diseases $9^{th}$ Edition Clinical Modification ("ICD-9") codes or International Classification of Diseases $10^{th}$ Edition Clinical Modification ("ICD-10") codes.

17. The system of claim 15 wherein the one or more generated electronic templates include one or more of an electronic invoice template, and electronic medical record template, a chief compliant template, a diagnosis template, a nurse template, a review template, or provider template.

* * * * *